(12) United States Patent
Chang et al.

(10) Patent No.: US 12,253,467 B2
(45) Date of Patent: Mar. 18, 2025

(54) DETERMINING PARTITION COEFFICIENTS OF TRACER ANALYTES

(71) Applicant: Saudi Arabian Oil Company, Dhahran (SA)

(72) Inventors: Sehoon Chang, Boston, MA (US); Gawain Thomas, Shirley, MA (US); Wei Wang, Quincy, MA (US); Hooisweng Ow, Woburn, MA (US)

(73) Assignee: Saudi Arabian Oil Company, Dhahran (SA)

( * ) Notice: Subject to any disclaimer, the term of this patent is extended or adjusted under 35 U.S.C. 154(b) by 36 days.

(21) Appl. No.: 17/643,983

(22) Filed: Dec. 13, 2021

(65) Prior Publication Data

US 2023/0184677 A1    Jun. 15, 2023

(51) Int. Cl.
| | |
|---|---|
| *G01N 21/64* | (2006.01) |
| *G01N 1/38* | (2006.01) |
| *G01N 33/18* | (2006.01) |

(52) U.S. Cl.
CPC ............... *G01N 21/64* (2013.01); *G01N 1/38* (2013.01); *G01N 33/18* (2013.01)

(58) Field of Classification Search
CPC ...... G03G 5/14704; G01N 1/38; G01N 21/64; G01N 33/18
See application file for complete search history.

(56) References Cited

U.S. PATENT DOCUMENTS

| | | | | |
|---|---|---|---|---|
| 1,529,349 | A | * | 3/1925 | Eddy ................... C10G 33/02 516/190 |
| 3,623,842 | A | | 11/1971 | Deans |
| 3,703,355 | A | | 11/1972 | Takahashi |
| 3,834,122 | A | | 9/1974 | Allison et al. |
| 3,851,171 | A | | 11/1974 | Saniford |
| 3,947,396 | A | | 3/1976 | Kangas et al. |
| 4,137,452 | A | | 1/1979 | Paap |
| 4,264,329 | A | | 4/1981 | Beckett |
| 4,289,203 | A | | 9/1981 | Swanson |
| 4,420,565 | A | | 12/1983 | Schmitt |

(Continued)

FOREIGN PATENT DOCUMENTS

| | | |
|---|---|---|
| AU | 2011284552 | 12/2013 |
| CA | 2997608 | 4/2017 |

(Continued)

OTHER PUBLICATIONS

Miaosi et al "Automated Femtoliter Droplet-Based Determination of Oil-Water Partition Coefficient" Anal. Chem. 2019, 91, 16, 10371-10375 (Year: 2019).*

(Continued)

*Primary Examiner* — Jennifer Wecker
*Assistant Examiner* — Jonathan Bortoli
(74) *Attorney, Agent, or Firm* — Fish & Richardson P.C.

(57) ABSTRACT

Optical properties of a tracer in water are measured at varying concentrations. A reference curve is built based on the measured optical properties at varying concentrations. An emulsion is mixed with the tracer. The emulsion is demulsified into an oil component and an aqueous component. Optical properties of one of the components are (Continued)

measured. A partition coefficient is determined based on the measured optical properties of a demulsified component and the reference curve.

10 Claims, 4 Drawing Sheets

(56) References Cited

U.S. PATENT DOCUMENTS

| | | | |
|---|---|---|---|
| 4,433,291 A | 2/1984 | Yariv et al. |
| 4,485,071 A | 11/1984 | Larter |
| 4,589,285 A | 5/1986 | Savit |
| 4,650,281 A | 3/1987 | Jaeger et al. |
| 4,694,046 A | 9/1987 | Bock et al. |
| 4,755,469 A | 7/1988 | Showalter |
| 4,772,563 A | 9/1988 | Evangelista et al. |
| 4,882,128 A | 11/1989 | Hukvari et al. |
| 4,882,763 A | 11/1989 | Buchan et al. |
| 4,976,270 A | 12/1990 | Parl et al. |
| 5,096,277 A | 3/1992 | Kleinerman |
| 5,124,268 A | 6/1992 | Dakubu |
| 5,168,927 A | 12/1992 | Stegenneier |
| 5,180,556 A | 1/1993 | Nolte et al. |
| 5,390,529 A | 2/1995 | Ghiselli |
| 5,441,343 A | 8/1995 | Pylkki et al. |
| 5,990,224 A | 11/1999 | Raynolds et al. |
| 6,095,679 A | 8/2000 | Hammiche et al. |
| 6,226,390 B1 | 5/2001 | Deruyter et al. |
| 6,250,848 B1 | 6/2001 | Moridis et al. |
| 6,252,016 B1 | 6/2001 | Wu et al. |
| 6,331,436 B1 | 12/2001 | Richardson |
| 6,380,534 B1 | 4/2002 | Mahmoud et al. |
| 6,488,872 B1 | 12/2002 | Beebe et al. |
| 6,491,425 B1 | 12/2002 | Hammiche et al. |
| 6,555,807 B2 | 4/2003 | Clayton et al. |
| 6,585,044 B2 | 7/2003 | Rester |
| 6,590,647 B2 | 7/2003 | Stephenson |
| 6,638,885 B1 | 10/2003 | McGrath et al. |
| 6,662,627 B2 | 12/2003 | Arnott et al. |
| 6,691,780 B2 | 2/2004 | Nguyen et al. |
| 6,939,515 B2 | 9/2005 | Carlson et al. |
| 7,032,662 B2 | 4/2006 | Malone |
| 7,033,975 B2 | 4/2006 | Baran, Jr. et al. |
| 7,086,484 B2 | 8/2006 | Smith |
| 7,249,009 B2 | 7/2007 | Ferworn et al. |
| 7,281,435 B2 | 10/2007 | Sale et al. |
| 7,289,942 B2 | 10/2007 | Yang et al. |
| 7,303,006 B2 | 12/2007 | Stone |
| 7,373,073 B2 | 5/2008 | Kamp et al. |
| 7,472,748 B2 | 1/2009 | Gdanski et al. |
| 7,485,471 B1 | 2/2009 | Sun et al. |
| 7,520,933 B2 | 4/2009 | Park et al. |
| 7,526,953 B2 | 5/2009 | Goodwin et al. |
| 7,588,827 B2 | 9/2009 | Nie et al. |
| 7,810,563 B2 | 10/2010 | Buijse et al. |
| 7,861,601 B2 | 1/2011 | Sale et al. |
| 7,875,654 B2 | 1/2011 | Hong et al. |
| 7,879,625 B1 | 2/2011 | Boss |
| 7,920,970 B2 | 4/2011 | Zuo et al. |
| 8,028,562 B2 | 10/2011 | Shah et al. |
| 8,062,418 B2 | 11/2011 | Costantz et al. |
| 8,148,477 B2 | 4/2012 | Saita et al. |
| 8,176,981 B2 | 5/2012 | Savu et al. |
| 8,177,422 B2 | 5/2012 | Kjoller et al. |
| 8,187,554 B2 | 5/2012 | Panagiotou |
| 8,269,501 B2 | 9/2012 | Schmidt et al. |
| 8,337,783 B2 | 12/2012 | Locascio et al. |
| 8,418,759 B2 | 4/2013 | Moore et al. |
| 8,507,844 B2 | 8/2013 | Mazza |
| 8,596,354 B2 | 12/2013 | Hartshorne et al. |
| 8,627,902 B2 | 1/2014 | Hammer |
| 8,629,089 B2 | 1/2014 | Dams |
| 8,638,104 B2 | 1/2014 | Barber et al. |
| 8,661,907 B2 | 3/2014 | Davis et al. |
| 8,722,812 B2 | 5/2014 | Yabu et al. |
| 8,816,689 B2 | 8/2014 | Colombo et al. |
| 8,821,806 B2 | 9/2014 | Hersherwitz et al. |
| 8,877,954 B2 | 11/2014 | Giesenberg et al. |
| 8,895,484 B2 | 11/2014 | Stray |
| 8,949,029 B2 | 2/2015 | Nyhavn |
| 8,969,261 B2 | 3/2015 | Talingting Pabalan et al. |
| 8,996,346 B2 | 3/2015 | Zuo et al. |
| 9,023,966 B2 | 5/2015 | Zhang et al. |
| 9,034,920 B2 | 5/2015 | Lam et al. |
| 9,050,655 B2 | 6/2015 | Chou et al. |
| 9,080,097 B2 | 7/2015 | Gupta et al. |
| 9,121,271 B2 | 9/2015 | Shook |
| 9,128,210 B2 | 9/2015 | Pomerantz |
| 9,133,709 B2 | 9/2015 | Huh et al. |
| 9,200,102 B2 | 12/2015 | Baran, Jr. et al. |
| 9,227,929 B2 | 1/2016 | Winter et al. |
| 9,279,771 B2 | 3/2016 | Aizenberg et al. |
| 9,284,833 B2 | 3/2016 | Hewitt et al. |
| 9,290,689 B2 | 3/2016 | Lafitte et al. |
| 9,296,851 B2 | 3/2016 | Luettgen |
| 9,322,056 B2 | 4/2016 | McCann et al. |
| 9,322,269 B2 | 4/2016 | Matherly et al. |
| 9,366,099 B2 | 6/2016 | Ly |
| 9,375,790 B2 | 6/2016 | Murphy et al. |
| 9,377,449 B2 | 6/2016 | Tour et al. |
| 9,481,764 B1 | 11/2016 | Kinlen et al. |
| 9,528,045 B2 | 12/2016 | Kanj et al. |
| 9,534,062 B2 | 1/2017 | He et al. |
| 9,592,555 B2 | 3/2017 | Schut et al. |
| 9,594,070 B2 | 3/2017 | Rule et al. |
| 9,624,422 B2 | 4/2017 | Dams et al. |
| 9,664,665 B2 | 5/2017 | Gisolf et al. |
| 9,696,270 B1 | 7/2017 | Roy et al. |
| 9,708,525 B2 | 7/2017 | Suresh et al. |
| 9,719,009 B2 | 8/2017 | Jangda et al. |
| 9,770,583 B2 | 9/2017 | Gupta et al. |
| 9,791,417 B2 | 10/2017 | Irisawa et al. |
| 9,809,740 B2 | 11/2017 | Chakraborty et al. |
| 9,873,622 B2 | 1/2018 | Kang et al. |
| 9,873,827 B2 | 1/2018 | Chakraborty et al. |
| 9,910,026 B2 | 3/2018 | Zhang et al. |
| 10,273,399 B2 | 4/2019 | Cox |
| 10,288,609 B2 | 5/2019 | Brueckner et al. |
| 10,308,865 B2 | 6/2019 | Cox |
| 10,308,895 B2 | 6/2019 | Vidal et al. |
| 10,316,873 B2 | 6/2019 | Weitz et al. |
| 10,392,555 B2 | 8/2019 | Giro et al. |
| 10,400,159 B2 | 9/2019 | Gupta |
| 10,421,894 B2 | 9/2019 | Johnson et al. |
| 10,436,003 B2 | 10/2019 | Kim et al. |
| 10,444,065 B2 | 10/2019 | Schmidt et al. |
| 10,458,207 B1 | 10/2019 | Matringe et al. |
| 10,487,259 B2 | 11/2019 | Cox |
| 10,611,967 B2 | 4/2020 | Inan |
| 10,858,931 B2 | 12/2020 | Chen et al. |
| 10,871,067 B2 | 12/2020 | Nyhavn |
| 10,895,497 B2 | 1/2021 | Schmidt et al. |
| 10,934,475 B2 | 3/2021 | Ren et al. |
| 10,961,443 B2 | 3/2021 | Zhao |
| 10,961,445 B2 | 3/2021 | Ogle et al. |
| 11,230,919 B2 | 1/2022 | Ow et al. |
| 2001/0036667 A1 | 11/2001 | Tayebi |
| 2002/0026000 A1 | 2/2002 | Varadaraj et al. |
| 2003/0220204 A1 | 11/2003 | Baran et al. |
| 2004/0108110 A1 | 6/2004 | Zupanick et al. |
| 2004/0143059 A1 | 7/2004 | Cabrera et al. |
| 2005/0080209 A1 | 4/2005 | Blankenship et al. |
| 2005/0252286 A1 | 11/2005 | Ibrahim et al. |
| 2006/0088476 A1 | 4/2006 | Harder |
| 2006/0105052 A1 | 5/2006 | Acar et al. |
| 2006/0120683 A1 | 6/2006 | Kamp et al. |
| 2007/0114030 A1 | 5/2007 | Todd et al. |
| 2007/0119244 A1 | 5/2007 | Goodwin et al. |
| 2007/0138401 A1* | 6/2007 | Tokhtuev .............. G01J 3/12 356/328 |
| 2008/0003142 A1* | 1/2008 | Link .............. B01L 3/502784 264/219 |
| 2008/0019921 A1 | 1/2008 | Zhang |
| 2008/0110253 A1 | 5/2008 | Stephenson et al. |

(56) References Cited

U.S. PATENT DOCUMENTS

| | | |
|---|---|---|
| 2008/0111064 A1 | 5/2008 | Andrews et al. |
| 2008/0206317 A1 | 8/2008 | Johnsson et al. |
| 2008/0220970 A1 | 9/2008 | Martin |
| 2009/0087911 A1 | 4/2009 | Rogerio |
| 2009/0087912 A1 | 4/2009 | Ramos et al. |
| 2009/0173253 A1 | 7/2009 | Roesch et al. |
| 2009/0174117 A1 | 7/2009 | Winkler et al. |
| 2009/0248309 A1 | 10/2009 | Nelville et al. |
| 2009/0253595 A1 | 10/2009 | Qu et al. |
| 2009/0264321 A1 | 10/2009 | Showalter et al. |
| 2009/0264768 A1 | 10/2009 | Courtney |
| 2009/0277625 A1 | 11/2009 | Bai et al. |
| 2010/0038086 A1 | 2/2010 | Bunnell et al. |
| 2010/0049625 A1 | 2/2010 | Biebesheimer et al. |
| 2010/0068821 A1 | 3/2010 | St Germain |
| 2010/0092865 A1 | 4/2010 | Kanno et al. |
| 2010/0200744 A1 | 8/2010 | Pearce et al. |
| 2010/0224823 A1 | 9/2010 | Yin et al. |
| 2010/0270020 A1 | 10/2010 | Baran et al. |
| 2010/0290999 A1 | 11/2010 | Kim |
| 2010/0305219 A1 | 12/2010 | Granick et al. |
| 2010/0307745 A1 | 12/2010 | Lafitte et al. |
| 2010/0314114 A1 | 12/2010 | Moradi-Araghi et al. |
| 2011/0012331 A1 | 1/2011 | Kim |
| 2011/0030949 A1 | 2/2011 | Weaver et al. |
| 2011/0129424 A1 | 6/2011 | Berkland et al. |
| 2011/0207231 A1 | 8/2011 | Natan et al. |
| 2011/0239754 A1 | 10/2011 | Dyer et al. |
| 2011/0257887 A1 | 10/2011 | Cooper et al. |
| 2011/0260051 A1 | 10/2011 | Preudhomme et al. |
| 2011/0275061 A1 | 11/2011 | Weidemaier et al. |
| 2011/0320128 A1 | 12/2011 | Shook |
| 2012/0026037 A1 | 2/2012 | Thomson et al. |
| 2012/0062886 A1 | 3/2012 | Piotti et al. |
| 2012/0092960 A1 | 4/2012 | Gaston et al. |
| 2012/0115128 A1 | 5/2012 | Miller |
| 2012/0135080 A1 | 5/2012 | Bromberg et al. |
| 2012/0175120 A1 | 7/2012 | Holcomb et al. |
| 2012/0190593 A1 | 7/2012 | Soane et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0017610 A1 | 1/2013 | Roberts et al. |
| 2013/0040292 A1 | 2/2013 | Lopez et al. |
| 2013/0084630 A1 | 4/2013 | Rolland et al. |
| 2013/0084643 A1 | 4/2013 | Commarieu et al. |
| 2013/0087020 A1 | 4/2013 | Brutchey et al. |
| 2013/0087329 A1 | 4/2013 | Hewitt et al. |
| 2013/0087340 A1 | 4/2013 | Choens et al. |
| 2013/0109261 A1 | 5/2013 | Koene |
| 2013/0126158 A1 | 5/2013 | Gupta |
| 2013/0172853 A1 | 7/2013 | McClain |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0036628 A1 | 2/2014 | Hill et al. |
| 2014/0048694 A1 | 2/2014 | Pomerantz |
| 2014/0060832 A1 | 3/2014 | Mahoney et al. |
| 2014/0077121 A1 | 3/2014 | Sun et al. |
| 2014/0120627 A1 | 5/2014 | Rubino et al. |
| 2014/0122047 A1 | 5/2014 | Saldivar et al. |
| 2014/0124196 A1 | 5/2014 | Sunde et al. |
| 2014/0159715 A1 | 6/2014 | McEwen-King |
| 2014/0186939 A1 | 7/2014 | Peterman et al. |
| 2014/0190700 A1 | 7/2014 | Tang et al. |
| 2014/0200511 A1 | 7/2014 | Boyden |
| 2014/0208825 A1 | 7/2014 | Holba et al. |
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |
| 2015/0001385 A1 | 1/2015 | Perriat et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0132742 A1 | 5/2015 | Thou et al. |
| 2015/0148269 A1 | 5/2015 | Tamsilian |
| 2015/0153472 A1 | 6/2015 | Tour |
| 2015/0159079 A1 | 6/2015 | Huh et al. |
| 2015/0175876 A1 | 6/2015 | Resasco et al. |
| 2015/0192436 A1 | 7/2015 | Farhadiroushan et al. |
| 2015/0218435 A1 | 8/2015 | Suresh et al. |
| 2015/0232747 A1 | 8/2015 | Kanj et al. |
| 2015/0232748 A1 | 8/2015 | Kanj et al. |
| 2015/0268370 A1 | 9/2015 | Johnston et al. |
| 2015/0299369 A1 | 10/2015 | Ausserre et al. |
| 2015/0337874 A1 | 11/2015 | Park |
| 2015/0368547 A1 | 12/2015 | Lesko et al. |
| 2015/0376493 A1 | 12/2015 | Huh et al. |
| 2016/0003040 A1* | 1/2016 | Jessheim ............. C09K 8/58 507/205 |
| 2016/0016166 A1 | 1/2016 | Rolland et al. |
| 2016/0040514 A1 | 2/2016 | Rahmani et al. |
| 2016/0061020 A1 | 3/2016 | Sayarpour |
| 2016/0061790 A1 | 3/2016 | Zhang |
| 2016/0075937 A1 | 3/2016 | Cannan |
| 2016/0083641 A1 | 3/2016 | Gamage |
| 2016/0097750 A1 | 4/2016 | Van Herzen et al. |
| 2016/0129371 A1 | 5/2016 | Black |
| 2016/0146662 A1 | 5/2016 | Stokely et al. |
| 2016/0215030 A1 | 7/2016 | Bressner |
| 2016/0251571 A1 | 9/2016 | Agrawal et al. |
| 2016/0264846 A1 | 9/2016 | Bennetzen et al. |
| 2016/0271513 A1 | 9/2016 | Weitz |
| 2016/0304934 A1 | 10/2016 | Matsuno |
| 2016/0340569 A1 | 11/2016 | Belcher |
| 2017/0022804 A1 | 1/2017 | Gupta et al. |
| 2017/0059668 A1 | 3/2017 | Chang et al. |
| 2017/0067322 A1 | 3/2017 | Wong |
| 2017/0173546 A1 | 6/2017 | Cheng et al. |
| 2017/0199124 A1 | 7/2017 | Bolduc et al. |
| 2017/0336528 A1 | 11/2017 | Badri et al. |
| 2017/0350236 A1 | 12/2017 | Shen et al. |
| 2017/0361376 A1 | 12/2017 | Murugesan et al. |
| 2018/0171782 A1 | 6/2018 | Cox et al. |
| 2018/0201644 A1 | 7/2018 | Kulak et al. |
| 2018/0275114 A1 | 9/2018 | Kosynkin et al. |
| 2018/0369808 A1 | 12/2018 | Wronko |
| 2019/0016943 A1 | 1/2019 | Ren et al. |
| 2019/0118175 A1 | 4/2019 | Kim et al. |
| 2019/0118265 A1 | 4/2019 | Nie et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2019/0374916 A1 | 12/2019 | Sherman et al. |
| 2019/0382648 A1 | 12/2019 | Murugesan et al. |
| 2020/0032641 A1 | 1/2020 | Kulyakhtin et al. |
| 2020/0116019 A1 | 4/2020 | Ow et al. |
| 2020/0290879 A1 | 9/2020 | Chang et al. |
| 2020/0377626 A1 | 12/2020 | Ow et al. |
| 2020/0408089 A1 | 12/2020 | Ow et al. |
| 2021/0018436 A1 | 1/2021 | Ow et al. |
| 2021/0025858 A1 | 1/2021 | Ow et al. |
| 2021/0080413 A1 | 3/2021 | Eichmann et al. |
| 2021/0080414 A1 | 3/2021 | Eichmann et al. |
| 2021/0107798 A1 | 4/2021 | Wang |
| 2021/0396907 A1 | 12/2021 | Wang |

FOREIGN PATENT DOCUMENTS

| | | |
|---|---|---|
| CA | 2941370 | 7/2018 |
| CA | 2916567 | 8/2019 |
| CN | 101475667 | 7/2009 |
| CN | 102649831 | 8/2012 |
| CN | 103160265 | 6/2013 |
| CN | 103267825 | 8/2013 |
| CN | 103275270 | 9/2013 |
| CN | 103352255 | 10/2013 |

(56) References Cited

FOREIGN PATENT DOCUMENTS

| | | |
|---|---|---|
| CN | 102586873 | 12/2014 |
| CN | 104616350 | 5/2015 |
| CN | 107915802 | 4/2018 |
| CN | 111303853 | 6/2020 |
| EA | 024705 | 10/2016 |
| EP | 0171978 | 11/1990 |
| EP | 1721603 | 11/2006 |
| EP | 2004573 | 12/2008 |
| EP | 2040075 | 3/2009 |
| EP | 2104082 | 9/2009 |
| EP | 1404776 | 11/2012 |
| EP | 2480625 | 4/2013 |
| EP | 2480626 | 4/2013 |
| EP | 3444028 | 2/2019 |
| FR | 2756046 | 5/1998 |
| FR | 2928484 | 9/2009 |
| GB | 2161269 | 8/1988 |
| GB | 2442745 | 4/2011 |
| GB | 2489714 | 10/2012 |
| JP | 2005524849 | 8/2005 |
| JP | 2007514169 | 5/2007 |
| JP | 2008505259 | 2/2008 |
| JP | 2008524602 | 7/2008 |
| JP | 2009535060 | 10/2009 |
| JP | 2009540326 | 11/2009 |
| JP | 2015523073 | 8/2015 |
| KR | 20170131731 | 11/2017 |
| KR | 101852925 | 4/2018 |
| TW | 200643094 | 12/2006 |
| WO | WO 1999038931 | 8/1999 |
| WO | WO 2002102917 | 12/2002 |
| WO | WO 2003100214 | 12/2003 |
| WO | WO 2004095259 | 11/2004 |
| WO | WO 2004113677 | 12/2004 |
| WO | WO 2007124814 | 11/2007 |
| WO | WO 2008034553 | 3/2008 |
| WO | WO 2010019256 | 2/2010 |
| WO | WO-2010121307 A1 * | 10/2010 .......... B01F 13/0062 |
| WO | WO 2010138914 | 12/2010 |
| WO | WO 2011035292 | 3/2011 |
| WO | WO 2011035294 | 3/2011 |
| WO | WO 2011063023 | 5/2011 |
| WO | WO 2011081681 | 7/2011 |
| WO | WO 2012052148 | 4/2012 |
| WO | WO 2012154332 | 11/2012 |
| WO | WO 2012158478 | 11/2012 |
| WO | WO 2013142869 | 9/2013 |
| WO | WO 2014008496 | 1/2014 |
| WO | WO 2014014919 | 1/2014 |
| WO | WO 2014066793 | 5/2014 |
| WO | WO 2014096495 | 6/2014 |
| WO | WO 2014100275 | 6/2014 |
| WO | WO 2014179020 | 11/2014 |
| WO | WO 2014207075 | 12/2014 |
| WO | WO 2015020642 | 2/2015 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2016174413 | 11/2016 |
| WO | WO 2017011328 | 1/2017 |
| WO | WO 2017015120 | 1/2017 |
| WO | WO 2017136641 | 8/2017 |
| WO | WO 2017164822 | 9/2017 |
| WO | WO 2017205565 | 11/2017 |
| WO | WO 2017210424 | 12/2017 |
| WO | WO 2018031655 | 2/2018 |
| WO | WO 2018085504 | 5/2018 |
| WO | WO 2018175763 | 9/2018 |
| WO | WO 2018234431 | 12/2018 |
| WO | WO 2019027817 | 2/2019 |
| WO | WO 2019063100 | 4/2019 |
| WO | WO 2020239649 | 12/2020 |
| WO | WO 2021092328 | 5/2021 |

OTHER PUBLICATIONS

Silva et al "Variation of the partition coefficient of phase-partitioning compounds between hydrocarbon and aqueous phases: an experimental study" May 2021 Fuel 300(01):120915 (Year: 2021).*

Theron et al "Comparison between three static mixers for emulsification in turbulent flow" International Jounral of Multiphase Flow vol. 37 N 5 pp. 488-500 (Year: 2011).*

Abed et al "Oil emulsions and the different recent demulsification techniques in the petroleum industry—A review" 2019 IOP Conf. Ser.: Mater. Sci. Eng. 702 012060 (Year: 2019).*

Jang ("Mathematical model for mixing in a paper-based channel and applications to the generation of a concentration gradient") International Journal of Heat and Mass Transfer, vol. 120, (Year: 2018).*

Marine ("Partition Coefficient Measurements in Picoliter Drops Using a Segmented Flow Microfluidic Device") Anal. Chem. 2009, 81, 1471-1476 (Year: 2009).*

Yokokawa (On-chip syringe pumps for picoliter-scale liquid manipulation) Lab Chip, 2006,6, 1062-1066 (Year: 2006).*

Lefferts ("Membranes as separators of dispersed emulsion phases") Agricultural University. Promotor(en): K. van 't Riet; M.A. Cohen Stuart; A. van der Padt.—Wageningen : Landbouwuniversiteit Wageningen—ISBN 9789054857099—157 https://library.wur.nl/WebQuery/wurpubs/39930 (Year: 1997).*

Wang ("A microfluidic-multiwell platform for rapid phase mapping of surfactant solutions"). Rev. Sci. Instrum. Apr. 1, 2020; 91 (4): 045109. https://doi.org/10.1063/1.5144770 (Year: 2020).*

Ma ("Elaboration of the Demulsification Process of W/O Emulsion with Three-Dimensional Electric Spiral Plate-Type Microchannel"). Micromachines 2019, 10, 751. https://doi.org/10.3390/mi10110751 (Year: 2009).*

Toxicity Estimation Software Tool (TEST) | US EPA (Year: 2008).*

Chao ("Automatic concentration and reformulation of PET tracers via microfluidic membrane distillation") Lab Chip. May 16, 2017; 17(10): 1802-1816. doi:10.1039/c6lc01569g. (Year: 2017).*

U.S. Appl. No. 17/454,176, filed Nov. 9, 2021, Wang et al.
U.S. Appl. No. 17/454,181, Wang et al., filed Nov. 9, 2021.
U.S. Appl. No. 17/522,437, Wang et al., filed Nov. 9, 2021.
U.S. Appl. No. 17/522,445, Wang et al., filed Nov. 9, 2021.
U.S. Appl. No. 17/548,837, Wang, filed Dec. 13, 2021.
U.S. Appl. No. 17/548,858, Wang, filed Dec. 13, 2021.
U.S. Appl. No. 17/549,062, Wang, filed Dec. 13, 2021.
U.S. Appl. No. 17/643,931, Wang, filed Dec. 13, 2021.

"Evolute Express User Guide," Biotage, 2016, Brochure, p. 3, p. 20-21, 36 pages.

"Method Development Guidelines: Solid Phase Extraction Using ISOLUTE® ENV+ for the Extraction of Aqueous Samples," Biotage, 2020, 3 pages.

"SPE columns, CHROMABOND HR-XAW, 85 μm, 1 mL/100 mg," Macherey-Nagel, available on or before Nov. 18, 2020, retrieved on Dec. 1, 2021, retrieved from URL <https://www.mn-net.com/us/spe-columns-chromabond-hr-xaw-85-m-1-ml/100-mg-730729>, 3 pages.

"Waters Corp Oasis WAX 6 cc Vac Cartridge, 500 mg Sorbent per Cartridge, 60 μm, 30/pk," Fisher Scientific, retrieved on Dec. 1, 2021, retrieved from URL <https://www.fishersci.com/shop/products/oasis-wax-cartridge-6cc-500mg/50466019>, 1 page.

"Optimizing Extraction of Multianalyte Suites from Water Samples Using Layered Solid Phase Extraction Columns," Biotage, Layered Solid Phase Extraction Columns, 2016, Brochure, 4 pages.

Agenet et al., "Fluorescent Nanobeads: a First Step Toward Intelligent Water Tracers," SPE-157019, Society of Petroleum Engineers (SPE), presented at the SPE International Oilfield Nanotechnology Conference held in Noordwijk, the Netherlands, Jun. 12-14, 2012, 13 pages.

Agilent "Agilent's New Mixed-Mode Anion Exchange Polymer Solid Phase Extraction Cartridges: SampliQ SAX," Agilent Technologies, Inc. 2008, Brochure, 4 pages.

Alfazazi et al., "Screening of New HPAM Base Polymers for Applications in High Temperature and High Salinity Carbonate Reservoirs," SPE-192805-MS, Society of Petroleum Engineers (SPE),

(56) References Cited

OTHER PUBLICATIONS presented at Abu Dhabi International Petroleum Exhibition & Conference, Nov. 12-15, 2018, 17 pages.

Allard and Larpent, "Core-shell type dually fluorescent polymer nanoparticles for ratiometric pH-sensing," J. Polym. Sci., Part A: Polym. Chem. 46:18 (6206-6213), 2008, 8 pages.

Alley et al., "Analysis of Polychlonnated Biphenyls in Fatty Biological Matrixes by On-Line Supercritical Fluid Extraction and Supercritical Fluid Cleanup." Journal of AOAC International 78.4, Jul. 1995, 1051-1054, 4 pages.

Al-Muntasheri et al., "Nanoparticle-Enhanced Hydraulic-Fracturing Fluids: A Review," SPE185161-PA, Society of Petroleum Engineers (SPE), SPE Production & Operations 32:02, May 2017, 10 pages.

Anbari et al., "Microfluidic Model Porous Media: Fabrication and Applications," Nano Micro Small, Special Issue: Multi-Scale Pores and Channels, May 3, 2018, 14:18 (1703575), 15 pages.

Angeles-Martinez, "Utilization of Water Salinity as a Continuous Miscible Tracer in Waterflooding." Paper presented at the SPE Latin America Petroleum Engineering Conference, Caracas, Venezuela, Mar. 1992, 7 pages.

Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.

Annen et al., "A facile synthesis of dispersible NaCl nanocrystals," Dalton Transactions, Nov. 2009, 44: 9731-9734, 5 pages.

Armelao et al., "Design of luminescent lanthanide complexes: From molecules to highly efficient photo-emitting materials," Coordination Chemistry Reviews, 254: 487-505, Mar. 2010, 19 pages.

Armstrong et al., "Artificial opal photonic crystals and inverse opal structures—fundamentals and applications from optics to energy storage," Journal of Materials Chemistry C, May 2015, 3: 6109-6143, 35 pages.

Asadi et al., "Application of Chemical Tracers in IOR: A Case History," SPE-126029-MS, Society of Petroleum Engineers (SPE), presented at the SPE North African Technical Conference and Exhibition, Feb. 14-17, 2010, 11 pages.

Asano et al., "Development of paper-based microfluidic analytical device for iron assay using photomask printed with 3D printer for fabrication of hydrophilic and hydrophobic zones on paper by photolithography," Analytica Chimica Acta, 883:55-60, Apr. 9, 2015, 6 pages.

Aslan et al., "Fluorescent Core—Shell AG@$SiO_2$ Nanocomposites for Metal-Enhanced Fluorescence and Single Nanoparticle Sensing Platforms," JACS Communications, J. Am. Chem. Soc. 129: 1524-1525, Jan. 19, 2007, 2 pages.

Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170: 390-397, 8 pages.

Badgett et al., "Totalsynthese eines Neobetanidin-Derivates und des Neobetenamins," Helvetica Chimica Acta 53(2): 433-448, 1970, 16 pages, English Summary.

Bagaria et al., "Iron Oxide Nanoparticles Grafted with Sulfonated Copolymers are Stable in Concentrated Brine at Elevated Temperatures and Weakly Adsorb on Silica," ACS Applied Materials & Interfaces, 5(8): 3329-3339, Mar. 25, 2013, 11 pages.

Bala et al., "Interaction of Different Metal Ions with Carboxylic Acid Group: A Quantitative Study," The Journal of Physical Chemistry A, 111(28): 6183-6190, Jun. 2007, 8 pages.

Bao et al., "Luminescence properties of the co-luminescence groups of Sm—La-pyridyl carboxylic acids," Journal of Rare Earths 30(4): 320-324, Apr. 2012, 5 pages.

Behnke et al., "Encapsulation of Hydrophobic Dyes in Polystyrene Micro- and Nanoparticles via Swelling Procedures." J. Fluoresc. 21(3): 937-944, 2011, 8 pages.

Benninger et al., "Time-resolved fluorescence imaging of solvent interaction in microfluidic devices," Optics Express, Sep. 2005, 11 pages.

Biot et al., "Temperature analysis in hydraulic fracturing," Journal of Petroleum Technology, vol. 39, No. 11, Nov. 1987, 9 pages.

Blachier et al., "Adsorption of polyamine on clay minerals" Journal of Colloid and Interface Science, 336, Aug. 2009, 599-606, 8 pages.

Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.

Borrini et al., "Water Soluble PDCA Derivatives for Selective Ln(III)/An(III) and Am(III)/Cm(III) Separation," Solvent Extraction and Ion Exchange 33(3): 224-235, Oct. 2014, 30 pages.

Boyjoo et al., "Synthesis of micro and nano-sized calcium carbonate particles and their applications," Journal of Materials Chemistry A, 2014, 2: 14270-14288, 19 pages.

Brichart et al., "The Use of Fluorescent Tracers for Inhibitor Concentration Monitoring Useful for Scale Inhibitor," IPTC-17933-MS, International Petroleum Technology Conference, presented at the International Petroleum Technology Conference held in Kuala Lumpur, Dec. 10-12, 2014, 8 pages.

Buchgraber et al., "Creation of a dual-porosity micromodel for pore-level visualization of multiphase flow," J. Petrol. Sci. Eng., 2012, 86-87: 27-38, 12 pages.

Bunzli and Piguet, "Taking advantage of luminescent lanthanide ions," Chemical Society Reviews, 34(12): 1048-1077, Sep. 2005, 30 pages.

Cahill et al., "Nanoscale Thermal Transport II," Applied Physics Reviews 1.1, 2014, 46 pages.

Cahill et al., "Nanoscale thermal transport," Journal of applied physics vol. 93, No. 2, Jan. 2003, 28 pages.

Cao et al., "Solute reactive tracers for hydrogeological applications: A short review and future prospects." Water 12.3, Mar. 2020, 21 pages.

Chang et al., "Magnetic SERS Composite Nanoparticles for Microfluidic Detection," 251st ACS National Meeting, Mar. 13-17, 2016, 1 pages, abstract only.

Chemspider.com [online], "Structure Search" Mar. 2008, [retrieved on Feb. 15, 2022], retrieved from : URL <http://www.chemspider.com/structuresearch.aspx>, 1 page.

Chen et al., "Aggregation Kinetics of Alginate-Coated Hematite Nanoparticles in Monovalent and Divalent Electrolytes," Environmental Science & Technology, 40(5): 1516-1523, Mar. 2006, 8 pages.

Chen et al., "Analysis of the solution conformations of T4 lysozyme by paramagnetic NMR spectroscopy," The Royal Society of Chemistry, Physical Chemistry Chemical Physics (PCCP) 18(8): 5850-5859, 2016, 10 pages.

Chen et al., "Hydration Repulsion between Carbohydrate Surfaces Mediated by Temperature and Specific Ions" Scientific Reports, vol. 6, Jun. 23, 2016, 10 pages.

Chen et al., "Impact of Irreversible Retention on Tracer Deployments; Constraining Novel Material Deployments," SPE 188890-MS, Society of Petroleum Engineers (SPE), presented at the SPE Abu Dhabi International Petroleum Exhibition and Conference, Nov. 2017, 8 pages.

Chen et al., "Improved Reservoir History Matching and Production Optimization with Tracer Data," SPE 191523-MS, Society of Petroleum Engineers (SPE), presented at the SPE Annual Technical Conference and Exhibition, Sep. 2018, 15 pages.

Chen et al., "Semicontinuous Monomer-Starved Emulsion Polymerization as a Means to Produce Nanolatexes: Analysis of Nucleation Stage," Langmuir, 29: 5650-5658, 2013, 9 pages.

Chen et al., "Synthesis of ordered lemellar supermicroporous silica with rigid neutral and long-chain cationic composite templating route," Plos One, Apr. 2019, 14(4): 3-5, 13 pages.

Chen et al., "Upconversion Nanoparticles: Design, Nanochemistry, and Applications in Theranostics" Chem. Rev, 114(10), Mar. 2014, 5161-5214, 54 pages.

Chen et al., "FITC functionalized magnetic core-shell $Fe_3O_4$/Ag hybrid nanoparticle for selective determination of molecular biothiols," Sensors and Actuators B: Chemical 193: 857-863, 2014, 7 pages.

Cheraghian, "Application of nano-particles of clay to improve drilling fluid" Int. J. Nanosci. Nanotechnol., 13, Jun. 2017, 177-186, 10 pages.

(56) References Cited

OTHER PUBLICATIONS

Christy et al., "Characterization of Natural Organic Matter by Pyrolysis/GC-MS," Environment International, 25, 1999, 9 pages.
Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.
Clark et al., "Water-Soluble Fluorochemical Surfactant Well Stimulation Additives," SPE9008, Society of Petroleum Engineers (SPE), Journal of Petroleum Technology, 34:07, Jul. 1982, 5 pages.
Clough et al., "Characterization of Kerogen and Source Rock Maturation Using Solid-State NMR Spectroscopy," Energy & Fuels, 2015, 29(10): 6370-6382, 42 pages.
Coates et al., "Enhancement of luminescence of europium(m) ions in water by use of synergistic chelation. Part 1.1:1 and 2:1 complexes," J. Chem. Soc, Perkin Trans. 2 (1275-1282), Jan. 1996, 8 pages.
Cole et al., "Polyethylene Glycol Modified, Cross-Linked Starch-Coated Iron Oxide Nanoparticles for Enhanced Magnetic tumor Targeting," Biomaterials, 32:8 (2183-2193), Mar. 1, 2011, 11 pages.
coleparmer.com [online] "Kinesis TELOS® Multilayer SPE Columns," Cole-Parmer, available on or before 2021, retrieved on Nov. 17, 2021, retrieved from URL<https://www.coleparmer.com/p/kinesis-telos-multilayer-spe-columns/71662>, 3 pages.
Constantin and Davidson, "Lamellar La mesophases doped with inorganicnanoparticles," MINIREVIEW, Chem. Phys. Chem. 15: 1270-1282, 2014, 12 pages.
Corning Incorporated, "12.10G1 Fluidic Modules Description," in 09-CD, MG1 HP Instruction Manual, 5 ed.; Corning, Ed. 78-79, 2016, 2 pages.
Corning, "The future flows through Corning Advanced Flow-Reactors," G1 Reactor. Corning, Ed. 2016, 3 pages.
Cox et al., "Pyrolyzable Nanoparticle Tracers for Environmental Interrogation and Monitoring," ACS Appl. Mater. Interfaces, 9(15), 13111-13120, 2017, 10 pages.
Cubillos et al., "The Value of Inter-well and Single Well Tracer Technology for De-Risking and Optimizing a CEOR Process—Caracara Field Case," SPE 174394-MS, Society of Petroleum Engineers (SPE), presented at the EUROPEC 2015, Jun. 1-4, 2015, 19 pages.
Cui et al., "A Combined Physical-Chemical Polymerization Process for Fabrication of Nanoparticle-Hydrogel Sensing Materials," Macromolecules 2012, 45 (20), 8382-8386, 5 pages.
Das et al., "Molecular Fluorescence, Phosphorescence, and Chemiluminescence Spectrometry," American Chemical Society (ACS Publications), Analytical Chemistry 84: S7-625, Nov. 3, 2011, 29 pages.
Deans, "Using Chemical Tracers To Measure Fractional Flow And Saturation In-Situ," SPE-7076, Society of Petroleum Engineers (SPE), presented at SPE Symposium on improved Methods of Oil Recovery, Apr. 16-17, 1978, 10 pages.
Deschamps et al., "Drilling to the Extreme: the Micro-Coring Bit Concept," IADC/SPE 115187, Society of Petroleum Engineers (SPE), International Association of Drilling Contractors (IADC), presented at the IADC/SPE Asia Pacific Drilling Technology Conference and Exhibition, Aug. 25-27, 2008, 12 pages.
Desmette et al., "Drilling Hard and Abrasive Rock Efficiently, or Generating Quality Cuttings? You No Longer Have to Choose . . . ," SPE 116554, Society of Petroleum Engineers (SPE), presented at the 2008 SPE Annual Technical Conference and Exhibition, Sep. 21-24, 2008, 19 pages.
Doda et al., "Investigation of Alkali Resistant Polymer for Improved Heavy Oil Recovery," SPE 165514, Society of Petroleum Engineers (SPE), presented at SPE Heavy Oil Conference—Canada, Jun. 11-13, 2013, 15 pages.
Du and Guan, "Interwell tracer tests: lessons learned from past field studies," Spe 93140-MS, Society of Petroleum Engineers (SPE), presented at the SPE Asia Pacific Oil and Gas Conference and Exhibition, Apr. 5-7, 2005, 9 pages.
Duan et al., "Review article: Fabrication of nanofluidic devices," Biomicrofluidics, Mar. 2013, 7:2 (026501), 42 pages.
Ducros, "Source Rocks of the Middle East," Source Rock Kinetics: Goal and Perspectives. AAPG Geosciences Technology Workshop, Jul. 2016, 30 pages.
Dugstad, "Chapter 6: Well-to-well tracer tests," in Petroleum Engineering Handbook, 5: 651-683, 2007, 31 pages.
Dung et al., "Structural and magnetic properties of starch coated magnetite nanoparticles" Journal of Experimental Nanoscience, 4, Sep. 2009, 259-267, 9 pages.
Edwards et al., "Extending the distance range accessed with continuous wave EPR with Gd3+ spin probes at high magnetic fields," The Royal Society of Chemistry, Physical Chemistry Chemical Physics (PCCP) 15:27 (11313-11326), 2013, 14 pages.
El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.
Esfahani et al., "Quantitative nanoscale mapping of three-phase thermal conductivities in filled skutterudites via scanning thermal microscopy," Nature Science Review, vol. 5, Issue 1, Feb. 2017, 31 pages.
Esmaeilzadeh et al., "Effect of ZrO2 nanoparticles on the interfacial behavior of surfactant solutions at airwater and n-heptane-water interfaces," Fluid Phase Equilibria, 2014, 361, 289-295, 7 pages.
Esumi et al., "Interaction between Zwitterionic Fluorocarbon and Anionic Surfactants in Aqueous Solutions," Langmuir, 9(358-360), 1993, 3 pages.
Fernández et al., "Evaluation of Cationic Water-Soluble Polymers With Improved Thermal Stability," SPE 93003, Society of Petroleum Engineers (SPE), presented at SPE International Symposium on Oilfield Chemistry, Society of Petroleum Engineers, Feb. 2005, 13 pages.
Fichtel et al., "A highly sensitive HPLC method for determination of nanomolar concentrations of dipicolinic acid, a characteristic constituent of bacterial endospores," Journal of Microbiological Methods, 2007, 70: 319-327, 9 pages.
Flury et al., "Dyes as tracers for vadose zone hydrology." Reviews of Geophysics 41.1, Mar. 2003, 37 pages.
Freeze and Cherry, "Chapter 9: Groundwater Contamination," in Groundwater, Englewood Cliffs, NJ: Prentice-Hall, Inc., 1979, 80 pages.
Gaillard et al., "New Water Soluble Anionic NVP Acrylamide Terpolymers for Use in Harsh EOR Conditions," SPE-169108-MS, Society of Petroleum Engineers (SPE), presented at SPE Improved Oil Recovery Symposium, Apr. 12-14, 2014, 18 pages.
Gaillard et al., "Selection of Customized Polymers to Enhance Oil Recovery from High Temperature Reservoirs," SPE-177073-MS, presented at the SPE Latin American and Caribbean Petroleum Engineering Conference, Society of Petroleum Engineers, Nov. 2015, 15 pages.
Galdiga and Greibrokk, "Ultra-trace determination of fluorinated aromatic carboxylic acids in aqueous reservoir fluids using solid-phase extraction in combination with gas chromatography-mass spectrometry," Journal of Chromatography A 793:2 (297-306), Jan. 16, 1998, 10 pages.
Gao et al., "A Surface Functional Monomer-Directing Strategy for Highly Dense Imprinting of TNT at Surface of Silica Nanoparticles," JACS Communications, Journal of American Chemical Society 129:25 (7859-7866), Jun. 2007, 8 pages.
Gardiner et al., "Chapter 1: Introduction to Raman Scattering," in Practical Raman Spectroscopy, Springer-Verlag, 1989, 9 pages.
Ge et al., "Fluorescence modified chitosan coated magnetic nanoparticles for high-efficient cellular imaging" Nanoscale Res. Lett, 4, Jan. 2009, 287-295, 9 pages.
George et al., "Modified Dipicolinic Acid Ligands for Sensitation and Europium (III) Luminescence," Inorganic Chemistry 45:4 (1739-1744), Feb. 1, 2006, 6 pages.
Georgi, et al., "Advances in Cuttings Collection and Analysis," SPWLA 34th Annual Logging Symposium, Jun. 13-16, 1993, 20 pages.
Gerami et al., "Microfluidics for Porous Systems: Fabrication, Microscopy and Applications," Transport in Porous Media, 2019, 130: 277-304, 28 pages.

(56) References Cited

OTHER PUBLICATIONS

Ghanem et al., "Investigation of Fluorescent Dyes as Partitioning Tracers for Subsurface Nonaqueous Phase Liquid (NAPL) Characterization," Journal of Environmental Engineering ASCE, Aug. 2003, 5 pages.

Goerke et al., "Analysis of the Transfer of Radical Co-polymerisation Systems from Semi-batch to Continuous Plants," in 12th International Symposium on Process Systems Engineering and 25th European Symposium on Computer Aided Process Engineering, Elsevier B.V, Copenhagen, Denmark, 2015, 6 pages.

Gogoi et al., "Review on microfluidic studies for EOR application," Journal of Petroleum Exploration and Production Technology, Sep. 2019, 9(3): 2263-2277, 15 pages.

Gordon-Grossman et al., "W-Band pulse EPR distance measurements in peptides using Gd3+− dipicolinic acid derivatives as spin labels," Physical Chemistry Chemical Physics 13:22 (10771-10780), 2011, 10 pages.

Greenkorn, "Experimental Study of Waterflood Tracers," SPE-169, Society of Petroleum Engineers (SPE), Journal Petroleum Technology, 14(1), Jan. 1962, 6 pages.

Grutzke et al., "Heptacoordinate Heteroleptic Salan (ONNO) and Thiosalan (OSSO) Titanium(IV) Complexes: Investigation of Stability and Cytotoxicity," American Chemical Society (ACS Publications), Inorganic Chemistry 54:14 (6697-6706), Jul. 2015, 10 pages.

Guo et al., "Crystallization in a Mixture of Solvents by Using a Crystal Modifier: Morphology Control in the Synthesis of Highly Monodisperse CaCO3 Microspheres," Angew. Chem. Int. Ed. 2006, 45:3977-3981, 5 pages.

Hagoot, "The response of interwell tracer tests in watered-out reservoirs," SPE 11131-MS, Society of Petroleum Engineers (SPE), presented at the 57th Annual Fall Technical Conference and Exhibition of the Society of Petroleum Engineers of AIME, Sep. 1982, 21 pages.

Han et al., "Application of Silver-Coated Magnetic Microspheres to a SERS-Based Optofluidic Sensor," American Chemical Society (ACS Publications), The Journal of Physical Chemistry (JPCC) 115: 6290-6296, Mar. 7, 2011, 7 pages.

Hansch et al., "Comparative QSAR: Understanding Hydrophobic Interactions," American Chemical Society, 1995, Chapter 19, 9 pages.

Hardy et al., "A novel fluorescent tracer for real-time tracing of clay transport over soil surfaces" Catena, 141, Jun. 2016, 39-45, 7 pages.

He et al., "Luminescent Europium Chelates Synthesis and Fluorescence Properties," Sensors and Materials 19:2 (123-132), 2007, 10 pages.

He et al., "One-pot Facile Synthesis of Janus Particles with Tailored Shape and Functionality," Electronic Supplementary Material (ESI) for Chemical Communications, The Royal Society of Chemistry, 2011, 17 pages.

Hindle et al., "Dipicolinic acid (DPA) assay revisited and appraised for spore detection," Analyst, 1999, 124: 1599-1604, 6 pages.

Holm et al., "Synthesis, Characterization, and Light-Induced Spatial Charge Separation in Janus Graphene Oxide," American Chemical Society (ACS Publications), Chemistry of Materials (CM) 30: 2084-2092, 2018, 9 pages.

hoteng.com [online], "Microfluidic Solutions for IOR/EOR Optimisation: Rapid and Cost Efficient EOR Screening using a Rock-On-A-Chip Approach," HOT Engineering GmbH, retrieved from URL <https://www.hoteng.com/microfluidic-solutions/#1457967643112-9de392c4-0c28>, retrieved on Jun. 2, 2020, available on or before Mar. 2019, 8 pages.

Hou et al., "Recent advances in colloidal photonic crystal sensors: Materials, structures and analysis methods," Nano Today, 2018, 22, 132-144, 13 pages.

Hu et al, "Fabrication, properties and applications of Janus particles," Chem. Soc. Rev. 41:11 (4356-4378), 2012, Feb. 2012, 23 pages.

Hu et al., "Smart Liquid SERS Substrates based on Fe3O4/Au Nanoparticles with Reversibly Tunable Enhancement Factor for Practical Quantitative Detection," Scientific Report 4: 7204 (1-10), Nov. 2014, 10 pages.

Huseby et al., "Assessing EOR potential from partitioning tracer data," SPE 172808-MS, Society of Petroleum Engineers (SPE), presented at the SPE Middle East Oil and Gas Show and Conference, Mar. 2015, 15 pages.

Huseby et al., "High Quality Flow Information from Tracer Data," SPE-169183-MS, Society of Petroleum Engineers (SPE), presented at the SPE Bergen One Day Seminar, Apr. 2, 2014, 9 pages.

Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.

Invitrogen, "Fluorophores and Their Amine-Reactive Derivatives" Molecular Probs Handbook, A Guide to Fluorescent Probes and Labeling Technologies, 11th Edition, 2010, 88 pages.

Jangda et al., "Evaluation of Fluorosurfactant Performance with Super-Critical CO2 Flooding for High Salinity Carbonate Reservoirs," SPE-169725-MS, presented at the SPE EOR Conference at Oil and Gas West Asia, Society of Petroleum Engineers, Mar. 2014, 14 pages.

Jenkins et al., "Ultratrace Determination of Selected Lanthanides by Luminescence Enhancement," Analytical Chemistry 68:17 (2974-2980), Sep. 1, 1996, 7 pages.

Jun et al., "Multifunctional Silver-Embedded Magnetic Nanoparticles as SERS Nanoprobes and Their Applications," Wiley-VCH Verlag Gmbh& Co. KGaA, Weinheim, Small 6:1 (119-125), Jan. 4, 2010, 7 pages.

Junkers, "Precision Polymer Design in Microstructured Flow Reactors: Improved Control and First Upscale at Once," Macromol. Chem. Phys. 218: 1600421-1600421, 2016, 9 pages.

Kaushik et al., "Gd(III) and Mn(II) complexes for dynamic nuclear polarization: small molecular chelate polarizing agents and applications with site-directed spin labeling of proteins," The Royal Society of Chemistry, Physical Chemistry Chemical Physics (PCCP) 18:39 (27205-27218), 2016, 36 pages.

Khalil et al., "Organic dye for subsea flowline assessment." SPE International Symposium on Oilfield Chemistry. OnePetro, Feb. 1999, 7 pages.

Khan et al., "Optimizing waterflood management in a giant UAE carbonate oil field using simulation-based streamlines," SPE 171777-MS, Society of Petroleum Engineers (SPE), presented at the Abu Dhabi International Petroleum Exhibition and Conference, Nov. 10-13, 2014, 9 pages.

Klapetek, "Chapter 11: Thermal Measurements," Quantitative Data Processing in Scanning Probe Microscopy: SPE Applications for Nanometrology, 2018, 26 pages.

Kneipp et al., "Single Molecule Detection Using Surface-Enhanced Raman Scattering (SERS)," Physical Review Letters, American Physical Society 78:9, Mar. 3, 1997, 4 pages.

Knowles et al., "Zwitterion Functionalized Silica Nanoparticle Coatings: The Effect of Particle Size on Protein, Bacteria, and Fungal Spore Adhesion," Langmuir, 35(5): 1335-1345, 2019, 11 pages.

Koelmans et al, "Chapter 12 in Marine Anthropogenic Litter" Springer Nature, 2015, 16 pages.

Kong et al., "Microfluidic diatomite analytical devices for illicit drug sensing with ppb-level sensitivity," Sensors and Actuators, B, 259, 2018, 9 pages.

Kornberger and Thiele, "Experiences with an Efficient Rate-Management Approach for the 8th Tortonian Reservoir in the Vienna Basin," SPE 166393-PA, Society of Petroleum Engineers (SPE), presented at the SPE Annual Technical Conference and Exhibition, Sep. 30-Oct. 2, 2013, SPE Reservoir Evaluation and Engineering 17:2, May 2014, 12 pages.

Kosynkin and Alaskar, "Oil Industry First Interwell Trial of Reservoir Nanoagent Tracers," SPE 181551-MS, Society of Petroleum Engineers (SPE), presented at the SPE Annual Technical Conference and Exhibition, Sep. 2016, 15 pages.

Kramer, "Water-Soluble Dendritic Architectures with Carbohydrate Shells for the Templation and Stabilization of Catalytically Active

(56) References Cited

OTHER PUBLICATIONS

Metal Nanoparticles," published by ACS, Macromolecules, 38:20 (8308-8315), Aug. 27, 2005, 8 pages.

Kulawardana et al., "Rheology and Transport of Improved EOR Polymers under Harsh Reservoir Conditions," SPE 154294, Society of Petroleum Engineers (SPE), presented at the SPE Improved Oil Recovery Symposium, Apr. 14-18, 2012, 14 pages.

Labbe et al., "Development of metal-chelating inhibitors for the Class II fructose 1,6-bisphosphate (FBP) aldolase," Journal of Inorganic Biochemistry 112: 49-58, Jul. 2012, 10 pages.

Lachowicz et al., "Biocompatible and fluorescent superparamagnetic iron oxide nanoparticles with superior magnetic properties coates with charged polysaccharide derivatives" Colloids and Surfaces B: Biointerfaces, 2017, 150, 402-407, 18 pages.

Larsen et al, "Efficient Synthesis of 4,7-Diamino Substituted 1,10-Phenanthroline-2,9-dicarboxamides," Organic Letters, 13:13 (3546-3548), Jul. 1, 2011, 3 pages.

Lee et al., "Site-Selective In Situ Grown Calcium Carbonate Micromodels with Tunable Geometry, Porosity, and Wettability," Advanced Functional Materials Interfaces, 2016, 10 pages.

Lehner et al., "Emergence of nanoplastic in the environment and possible impact on human health." Environmental science & technology 53.4, Jan. 2019, 1748-1765, 18 pages.

Levitt et al., "Selection and Screening of Polymers for Enhanced-Oil Recovery," SPE 113845, Society of Petroleum Engineers (SPE), presented at the SPE Symposium on Improved Oil Recovery, Apr. 19-23, 2008, 18 pages.

Lewan, "Evaluation of petroleum generation by hydrous pyrolysis experimentation," Phil. Trans. R. Soc. Lond. A, 1985, 315: 123-134, 13 pages.

Lewan, "Experiments on the role of water in petroleum formation," Geochimica et Cosmochimica Acta, Pergamon, 1997, 61:17 (3691-3723), 33 pages.

Li et al., "An amino-endcapped octadecylsilane silica-based mixed-mode stationary phase for the simultaneous separation of neutral and ionizable components in fixed-dose combinations." Analytical Methods 11.30, 2019, 3898-3909, 12 pages.

Li et al., "Automated Femtoliter Droplet-Based Determination of Oil-Water Partition Coefficient," Anal. Chem., 91, 10371, 2019, 5 pages.

Li et al., "Long persistent phosphors—from fundamentals to applications" Chem. Soc. Rev., 45(8), Apr. 2016, 2090-2136, 48 pages.

Li et al., "Magic Angle Spinning NMR Structure Determination of Proteins from Pseudocontact Shifts," JACS Communications, Journal of the American Chemical Society 135:22 (8294-8303), May 2013, 10 pages.

Li et al., "Superparamagnetic Iron Oxide Nanoparticles as MRI contrast agents for Non-invasive Stem Cell Labeling and Tracking" Theranostics, Jul. 2013, 3(8):595-615, 21 pages.

Li et al., "Thiol-ene reaction: a versatile tool in site-specific labelling of proteins with chemically inert tags for paramagnetic NMR," The Royal Society of Chemistry, Chemical Communications, Cambridge, United Kingdom 48:21 (2704-2706), 2012, 18 pages.

Liang et al., "Janus hollow spheres by emulsion interfacial self-assembled sol-gel process," Chemical Communications, Jan. 2011, 47(4): 1231-1233, 3 pages.

Liu et al, "Biological regeneration of manganese (IV) and iron (III) for anaerobic metal oxide-mediated removal of pharmaceuticals from water" Chemosphere 208, May 2018, 122-130, 43 pages.

Liu et al., "Photostimulated near-infrared persistent luminescence as a new optical read-out from Cr3+− doped LiGa5O8" Scientific Reports 3, Article 1554, Mar. 2013, 9 pages.

Liu et al., "Separation of polyethylene glycols and their fluorescein-labeled compounds depending on the hydrophobic interaction by high-performance liquid chromatography." Journal of Chromatography A 1129.1, Sep. 2006, 61-66, 6 pages.

Lomstein and Jorgensen, "Pre-column liquid chromatographic determination of dipicolinic acid from bacterial endospores," Limnology and Oceanography: Methods, Apr. 2012, 10:4, 227-233, 14 pages.

Lu et al., "Quantitative prediction of seismic rock physics of hybrid tight oil reservoirs of the Permian Lucaogou Formation, Junggar Basin, Northwest China," Journal of Asian Earth Sciences, 2019, 178: 216-223, 8 pages.

Luo et al., "Nanofluid of graphene-based amphiphilic Janus Nanosheets for tertiary or enhanced oil recovery: high performance at low concentration," Proceedings of the National Academy of Sciences of USA, PNAS, vol. 113, No. 28, Jul. 12, 2016, 17 pages.

Luo et al., "Secondary Oil Recovery Using Graphene-Based Amphiphilic JanusNanosheet Fluid at an Ultralow Concentration," American Chemical Society (ACS Publications), Industrial & Engineering Chemistry Research (I&EC Research), 56: 11125-11132, Sep. 2017, 25 pages.

Mahdavi et al., "Preparation, Characterization, and Application of Polyacrylamide-Polystyrene/Bentonite Nanocomposite as an Effective Immobilizing Adsorbent for Remediation of Soil" Chemistry Select, 5, Apr. 2020, 4538-4547, 12 pages.

Mahmoudi et al., "Superparamagnetic iron oxide nanoparticles development surface modification and applications in chemotherapy" Advanced Drug Delivery Reviews, Jan. 2011, 63, 24-46, 23 pages.

Manna et al., "Complexation behavior of trivalent actinides and lanthanides with 1,10-phenanthroline-2,9-dicarboxylic acid based ligands: insight from density functional theory," Physical Chemistry Chemical Physics (PCCP) 14:31 (11060), Jan. 1, 2012, 10 pages.

Mao et al., "Chemical and nanometer-scale structure of kerogen and its change during thermal maturation investigated by advanced solid-state 13C NMR spectroscopy," Geochimica et Cosmochimica Acta, 2010, 74(7): 2110-2127, 18 pages.

Marais et al., "Time-Resolved Fluorescence for Real-Time Monitoring of Both Scale and Corrosion Inhibitors: a Game-Changing Technique," SPE 179867, Society of Petroleum Engineers (SPE), presented at the SPE International Oilfield Scale Conference and Exhibition held in Aberdeen, Scotland, May 11-12, 2016 11 pages.

Marchetti et al., "Fluorous affinity chromatography for enrichment and determination of perfluoroalkyl substances," American Chemical Society (ACS Publications), Annual Review of Analytical Chemistry 84: 7138-7145, Jul. 19, 2012, 8 pages.

Marine et al., "Partition Coefficient Measurements in Picoliter Drops Using a Segmented Flow Microfluidic Device," Anal. Chem., 81, 1471, 2009, 6 pages.

Martinez et al., "Chapter 9: Polysaccharide-based Nanoparticles for Controlled Release Formulations," in The Delivery of Nanoparticles, 185-222, May 2012, 39 pages.

Martini et al., "How to Monitor Scale Inhibitor Squeeze using Simple TRF Tracers," SPE-173768-MS, Society of Petroleum Engineers (SPE), presented at the SPE International Symposium on Oilfield Chemistry held in the Woodlands, Texas, Apr. 13-15, 2015, 8 pages.

Mattsson et al., "Nanoplastics in the aquatic environment." Microplastic contamination in aquatic environments, Jan. 2018, 379-399, 11 pages.

McGrail et al., "Selective mono-facial modification of grapheneoxide nanosheets in suspension," The Royal Society of Chemistry, Chem. Commun, 52: 288-291, 2016, 5 pages.

McWilliams et al., "Fluorescent surfactants from common dyes—rhodamine B and eosin Y." Pure and Applied Chemistry 92.2, Feb. 2020, 265-274, 15 pages.

Melton et al., "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study," Inorganic Chemistry 45:23 (9306-9314), Nov. 1, 2006, 9 pages.

Meyer et al., "Identification of Source Rocks on Wireline Logs by Density/Resistivity and Sonic Transit Time/Resistivity Crossplots," AAPG Bulletin, 1984, 68(2): 121-129, 9 pages.

Micronit Microfluidics BV., "Example chip drawing," retrieved on May 9, 2008, retrieved from URL <https://www.micronit.com>, 1 page.

Micronit.com [online], "Enhanced oil recovery," retrieved from URL <https://www.micronit.com/products/enhanced-oil-recovery.html>, retrieved on Mar. 10, 2020, 5 pages.

(56) References Cited

OTHER PUBLICATIONS

Micronit.com [online], "Lab-on-a-chip and MEMS Solutions," retrieved from URL <https://www.micronit.com/>, retrieved on Jun. 2, 2020, available on or before Mar. 19, 2018 via wayback machine URL <https://web.archive.org/web/20180319182410/https://www.micronit.com/>, 7 pages.

Miller and McQuade, "5 Synthesis of Materials I Flow—Principles and Practice," in De Gruyter et al., Flow Chemistry, 2: 133-160, 2014, Part II, Chapter 5, 28 pages.

Mohamed et al., "Reaction screening in continuous flow reactors," J. Tetrahedron Letters, 57: 3965-3977, 2016, 12 pages.

Morse et al., "Enhanced Reaction Efficiency in Continuous Flow," Isr. J. Chem, 57:218-227, Apr. 2017, 14 pages.

Moyner et al., "The Application of Flow Diagnostics for Reservoir Management," Society of Petroleum Engineers (SPE), SPE Journal, Apr. 2015, 18 pages.

Muller and Seubert, "Ultra trace determination of fluorobenzoic acids in tap and reservoir water using solid-phase extraction and gas chromatography-mass spectrometry," Journal of Chromatography A, 1260: 9-15, Oct. 2012, 7 pages.

Musyanovych et al., "Preparation of Biodegradable Polymer Nanoparticles by Miniemulsion Technique and Their Cell Interactions," Macromolecular Bioscience, 8:2, Feb. 11, 2008, 13 pages.

Nahum et al., "Evaluation of Octanol-Water Partition Coefficients By Using High-Performance Liquid Chromatography," Journal of Chromatography, Elsevier Scientific Publishing Company, 1980, 192: 315, 8 pages.

Namwong et al., "Fabricating Simple Wax Screen-Printing Paper-Based Analytical Devices to Demonstrate the Concept of Limiting Reagent in Acid-Base Reactions," Journal of Chemical Education 95:2, 2018, 5 page.

Negin et al., "Application of nanotechnology for enhancing oil recovery—A review," Ke Ai Advanced Research Evolving Science, Petroleum 2: 324-333, 2016, 10 pages.

Negin et al., "Most common surfactants employed in chemical enhanced oil recovery," Petroleum 3: 197-211, 2017, 32 pages.

Ng et al., "Graphene-based two-dimensional Janus materials," NPG Asia Materials 10:4 (217-237), Apr. 2018, 21 pages.

Nge et al., "Advances in Microfluidic Materials, Functions, Integration, and Applications," Chem. Rev., Apr. 2013, 113, 2550-258, 34 pages.

Nguyen et al., "Separation and analysis of microplastics and nanoplastics in complex environmental samples" Acc Chem Res 52(4), Mar. 2019, 858-866, 23 pages.

Nie et al., "Probing Single Molecules and Single Nanoparticles by Surface-Enhanced Raman Scattering," Science 275:5303 (1102-1106), Feb. 21, 1997, 6 pages.

Nikonov et al., "Development of Remote Gas Condensate Fields: Challenges and Solutions," SPE 176660-MS, Society of Petroleum Engineers (SPE), SPE Russian Petroleum Technology Conference, Oct. 26-28, 2015, published Jan. 1, 2015, 21 pages.

Nödler et al., "Polar organic micropollutants in the coastal environment of different marine systems." Marine Pollution Bulletin 85.1, Aug. 2014, 50-59, 10 pages.

Ogden et al, "Complexation of Am(III) and Nd(in) by 1,10-Phenanthroline-2,9-Di carboxylic Acid," Journal of Solution Chemistry 42:1 (211-225), 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry 41:6 (1436-1445), Feb. 2002, 10 pages.

Ow, et al, "First Deployment of a Novel Advanced Tracers System for Improved Waterflood Recovery Optimization ," SPE-192598, Society of Petroleum Engineers, Nov. 2018, 10 pages.

Pallenberg et al. "Synthesis and Characterization of Some Copper(I) Phenanthroline Complexes," Inorg. Chem. 34: 2833-2840, 1995, 8 pages.

Park et al., "Application of montmorillonite in bentonite as a pharmaceutical excipient in drug delivery systems" Journal of Pharmaceutical Investigation, 46, May 2016, 363-375, 13 pages.

Parker and Williams, "Getting excited about lanthanide complexation chemistry," Journal of the Chemical Society, Dalton Transactions, 18: 3613-3628, 1996, 16 pages.

Parker et al., "Being excited by lanthanide coordination complexes: aqua species, chirality, excited-state chemistry, and exchange dynamics," Chemical Reviews, 102:6 (1977-2010), May 2002, 34 pages.

Peng et al., "A review of nanomaterials for nanofluid enhanced oil and recovery," The Royal Society of Chemistry, RSC Advances 7: 32246-32254, Jun. 13, 2017, 9 pages.

Peng, et al, "Micro- and nano-plastics in marine environment: Source, distribution and threats—A review" Sci. Total Environ, 698, 134254, 2020, 12 pages.

Petoud et al., "Brilliant SM, Eu, Tb, and Dy Chiral Lanthanide Complexes with Strong Circularly Polarized Luminescence," JACS Communications, Journal of the American Chemical Society 2017:129 (77-83), Dec. 15, 2006, 7 pages.

Pollock and Hammiche, "Micro-thermal analysis: techniques and applications," Journal of Physics D: Applied Physics, vol. 34.9, 2001, 31 pages.

Potapov et al., "Nanometer-Scale Distance Measurements in Proteins Using Gd3+ Spin Labeling," Journal of the American Chemical Society, 132(26): 9040-9048, Jun. 2010, 9 pages.

Qianming et al., "Bspda Synthesis and its Europium (III) Complexes' Fluorescence," Chemical Industry Times, Jul. 2005, 19(7): 38-41, 4 pages (English Abstract).

Quadri et al., "Screening of Polymers for EOR in High Temperature, High Salinity and Carbonate Reservoir Conditions," IPTC-18436-MS, presented at the International Petroleum Technology Conference (IPTC), Dec. 6-9, 2015, 30 pages.

Rashadan et al., "Effect of the preparation route, PEG and annealing on the phase stability of Fe3O4 nanoparticles and their magnetic properties," Journal of Experimental Nanoscience 8(2): 210-222, 2013, 14 pages.

Reese et al., "Synthesis of Highly Charged, Monodisperse Polystyrene Colloidal Particles for the Fabrication of Photonic Crystals," Colloid and Interface Science, 2000, 232: 76-80, 5 pages.

Reisch and Klymchenko, "Fluorescent Polymer Nanoparticles Based on Dyes: Seeking Brighter Tools for Bioimaging." Small 12(15): 1968-1992 2016, 25 pages.

Renault et al., "Three-Dimensional Wax Patterning of Paper Fluidic Devices," Langmuir, 30:23, 2014, 7 pages.

Ritter et al., "Octanol/Water Partition Coefficients for Environmentally Important Organic Compounds, " Environ. Sci & Pollut. Res. 1995, 2, 153-160, 8 pages.

Rovani, "Enhanced Oil Recovery: Aqueous Flow Tracer Measurement" WRI-09-R002, OSTI.Gov, Technical Report, U.S. Department of Energy, Feb. 2009, 1-18, 25 pages.

Rovani, Jr. and Schabron, "Enhanced Oil Recovery: Aqueous Flow Tracer Measurement,".

Rowan et al., "Dynamic Covalent Chemistry," Angewante Chemie International Edition 41: 898-952, Mar. 15, 2002, 55 pages.

Rubasinghege et al., "Abiotic degradation and environmental toxicity of ibuprofen: Roles of mineral particles and solar radiation." Water research 131, Mar. 2018, 22-32, 11 pages.

Sabbatini et al., "Luminescent lanthanide complexes as photochemical supramolecular devices," Coordination Chemistry Reviews, 123:1-2 (201-228), Feb. 1993, 28 pages.

Sabhapondit et al., "Water Soluble Acrylamidomethyl Propane Sulfonate (AMPS) Copolymer as an Enhanced Oil Recovery Chemical," Energy & Fuels, 17:683-688, 2003, 6 pages.

Saeki et al., "Upper and lower critical solution temperatures in poly (ethylene glycol) solutions," Polymer, 17(8): 685-689, Aug. 1976, 5 pages.

Sajjadi, "Nanoparticles Formation by Monomer-Starved Semibatch Emulsion Polymerization," Langmuir, 23: 1018-1024, 2007, 7 pages.

Sajjadi, "Particle Formation under Monomer-Starved Conditions in the Semibatch Emulsion Polymerization of Styrene. I. Experimental.," Journal of Polymer Science: Part A: Polymer Chemistry, 39: 3940-3952, 2001, 13 pages.

(56) References Cited

OTHER PUBLICATIONS

Sammes and Yshioglu, "Modern bioassays using metal chelates as luminescent probes," Natural Product Reports, 31:1, 1996, 28 pages.

Sanni et al., "A field case study of inter-well chemical tracer test," SPE-173760-MS, Society of Petroleum Engineers (SPE), in SPE International Symposium on Oilfield Chemistry, Apr. 2015, 17 pages.

Sanni et al., "Pushing the envelope of residual oil measurement: A field case study of a new class of inter-well chemical tracers," Journal of Petroleum Science and Engineering 163, 2018, 19 pages.

Santarelli et al., "Formation Evaluation From Logging on Cuttings," SPE 36851, Society of Petroleum Engineers (SPE), presented at the 1996 SPE Permian Basin Oil and Gas Recovery Conference, Mar. 27-29, 1996, SPE Reservoir Evaluation and Engineering, published Jun. 1998, 7 pages.

Schmidt et al., "Copper dipicolinates as peptidomimetic ligands for the Src SH2 domain," Bioorganic & Medicinal Chemistry Letters, 14(16), 4203-4206, Aug. 2004, 4 pages.

Schmidt et al., "Synthesis of Mono- and Dinuclear Vanadium Complexes and Their Reactivity toward Dehydroperoxidation of Alkyl Hydroperoxides," Inorganic Chemistry 56(3): 1319-1332, 2017, 14 pages.

Seah et al., "Optimizing Recovery in Gas Condensate Reservoirs," SPE 171519-MS, Society of Petroleum Engineers (SPE), SPE Asia Pacific Oil and Gas Conference and Exhibition, Oct. 16, 2014, 19 pages.

Selvin et al., "Principles and biophysical applications of lanthanide-based probes," Annual Review of Biophysics and Biomolecular Structure 31: 275-302, Jun. 2002, 28 pages.

Serres-Piole et al., "Direct sensitive simultaneous determination of fluorinated benzoic acids in oil reservoir waters by ultra high-performance liquid chromatography-tandem mass spectrometry" Journal of Chromatography A, 1218, Aug. 2011, 6 pages.

Serres-Piole et al., "Water tracers in oilfield applications: Guidelines," Elsevier Ltd., Journal of Science and Engineering 98-99: 22-39, Nov. 2012, 18 pages.

Shamsijazeyi et al., "Polymer-Coated Nanoparticles for Enhance Oil Recovery," Journal of Applied Polymer Science, 131:15, Aug. 5, 2014, 13 pages.

Sharma and Mohanty, "Wettability Alteration in High-temperature and High-salinity Carbonate Reservoirs," SPE 147306, Society of Petroleum Engineers (SPE), presented at the SPE Annual Technical Conference and Exhibition, Oct. 30-Nov. 2, 2011, SPE Journal 18:4 (646-655), Aug. 2013, 10 pages.

Shook et al., "Determining Reservoir Properties and Flood Performance from Tracer Test Analysis," SPE 124614, Society of Petroleum Engineers (SPE), presented at SPE Annual Technical Conference and Exhibition, Oct. 4-7, 2009, 19 pages.

sigmaaldrich.com [online] "pk20 Envicarb/LC-NH2/Si SPE Tubes 20m," Millapore Sigma, available on or before 2021, retrieved on Nov. 17, 2021, retrieved from URL <https://www.sigmaaldrich.com/US/en/product/supelco/54036u?context=product>, 4 pages.

sigmaaldrich.com [online] "Supelclean™ ENVI-Carb/NH2 SPE Tube," Millipore Sigma, available on or before 2021, retrieved on Nov. 17, 2021, retrieved from URL <https://www.sigmaaldrich.com/US/en/substance/supelcleanenvicarbnh2spetube1234598765?context=product>, 2 pages.

sigmaaldrich.com [online] "Supelclean™ SPE Method Development Kit," Millipore Sigma, available on or before 2021, retrieved on Nov. 17, 2021, retrieved from URL <https://www.sigmaaldrich.com/US/en/product/supelco/57074u?context=product>, 4 pages.

Silva et al., "Studies on New Chemical Tracers for Determination of Residual Oil Saturation in the Inter-Well Region," SPE-185085-MS, Society of Petroleum Engineers, 2017.

Silva et al., "Studies on new chemical tracers for determination of residual oil saturation in the inter-well region." SPE-185085-MS, SPE Oklahoma City Oil and Gas Symposium. OnePetro, Mar. 2017, 14 pages.

Silva et al., "Variation of the partition coefficient of phase-partitioning compounds between hydrocarbon and aqueous phases: an experimental study," Fuel, 300(120915), 2021, 15 pages.

Singh et al., "Paper-based sensors: emerging themes and applications," Sensors, 18:9, 2018, 22 pages.

Sobeih et al., "Recent trends and developments in pyrolysis-gas chromatography," Journal of Chromatography A, 1186:1-2 (51-66), Oct. 11, 2007, 16 pages.

Solomon et al., "Synthesis and Study of Silver Nanoparticles," Journal of Chemical Education 84(2): 332-325, 2007, 4 pages.

Song et al., "SERS-Encoded Nanogapped Plasmonic Nanoparticles: Growth of Metallic Nanoshell by Templating Redox-Active Polymer Brushes," JACS Communications, Journal of the American Chemical Society 136: 6838-6841, Apr. 28, 2014, 4 pages.

Speltini et al., "Newest applications of molecularly imprinted polymers for extraction of contaminants from environmental and food matrices: A review." Analytica Chimica Acta 974, Jun. 2017, 26 pages.

Sriram et al., "Paper-based microfluidic analytical devices for coloimetric detection of toxic ions," Trends in Analytical Chemistry, 93, Jun. 2017, 43 pages.

Stein et al., "Design and functionality of colloidal-crystal-templated materials-chemical applications of inverse opals," Chem. Soc. Rev., 2013, 42: 2763-2803, 41 pages.

Stephan et al., "Continuous-flow microfluidic method for octanol-water partition coefficient measurement," [Fluid Phase Equilibria 380: 116, 2014, 5 pages.

Stiles et al., "Surface-Enhanced Raman Spectroscopy," Annual Review of Analytical Chemistry 1: 601-626, Mar. 18, 2008, 29 pages.

Stryer et al., "Diffusion-enhanced fluorescence energy transfer," Annual Review of Biophysics and bioengineering 11:1, 1982, 21 pages.

Su et al., "A Dipicolinic Acid Tag for Rigid Lanthanide Tagging of Proteins and Paramagnetic NMR Spectroscopy," Journal of the American Chemical Society, 130:32 (10486-10487), Jul. 2008, 2 pages.

Sui, et al, "Occurrence, sources and fate of pharmaceuticals and personal care products in the groundwater: A review" Emerging Contaminants, vol. 1, Issue 1, Nov. 2015, 14-24, 11 pages.

Sýkora et al., "Recent advances in mixed-mode chromatographic stationary phases." Journal of separation science 42.1, Jan. 2019, 89-129, 75 pages.

Tabatabaei et al., "Well performance diagnosis with temperature profile measurements," in SPE Annual Technical Conference and Exhibition, Society of Petroleum Engineers, Oct. 30-Nov. 2, 2011, published Jan. 2011, 16 pages.

Takenaka et al., "Effect of fatty acids on the membrane fluidity of cultured chick dorsal root ganglion measured by fluorescence photobleaching recovery." Journal of neurobiology 14.6, Nov. 1983, 457-461, 5 pages.

Tang et al., "Synthesis and fluorescence properties of Tb(III) complexes with pyridine-2,6-dicarboxylic acid derivatives," Journal of Central South University of Technology (English Edition) 15:5 (599-605), Oct. 2008, 7 pages.

Tang et al., "Synthesis of Novel Derivatives of Pyridine-2,6-dicarboxylic Acid," Synthetic Communications: An International Journal for Rapid Communication of Synthetic Organic Chemistry 36:14 (2027-2034), Jun. 2006, 9 pages.

Tang et al., "Synthesis of Eu(III) and Tb(III) Complexes with Novel Pyridine-2,6-Dicarboxylic Acid Derivatives and Their Fluorescence Properties," Front. Chem. China 4: 408-413, 2006, 6 pages.

Tathed et al., "Hydrocarbon saturation in Bakken Petroleum System based on joint inversion of resistivity and dielectric dispersion logs," Fuel, Dec. 2018, 233: 45-55, 11 pages.

Taylor et al., "Water-Soluble Hydrophobically Associating Polymers for Improved Oil Recovery: A Literature Review," SPE 29008, Society of Petroleum Engineers (SPE), Journal of Petroleum Science and Engineering, 19:3-4 (265-280), Mar. 1998, 16 pages.

Teledyne Princeton Instruments, "PI-MAX 4: 1024 EMB," Datasheet, available on or before May 13, 2020, retrieved from URL <https://www.princetoninstruments.com/products/pi-max-family>, 8 pages.

(56) References Cited

OTHER PUBLICATIONS

Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.

Tian et al., "Off-Resonant Gold Superstructures as Ultrabright Minimally Invasive Surface-Enhanced Raman Scattering (SERS) Probes," American Chemical Society (ACS Publications), Chemistry of Materials (CM) 27: 5678-5684, Jul. 2015, 7 pages.

Toulhoat, "Experimentation and Modelling of U, Th and Lanthanides Transport in Fissured Rocks: Influence of Complexation," MRS Proceedings 50, Jan. 1, 1985, 8 pages.

Trippetta et al., "The seismic signature of heavy oil on carbonate reservoir through laboratory experiments and AVA modelling," Journal of Petroleum Science and Engineering, 2019, 177: 849-860, 12 pages.

Vaccaro et al., "Flow Approaches Towards Sustainability," Green Chem, 16:3680-3704, 2014, 25 pages.

Vatanparast et al., "Wettability alteration of low-permeable carbonate reservoir rocks in presence of mixed ionic surfactants," Petroleum Science and Technology 29:18 (1873-1884), 2011, 14 pages.

Vermolen et al., "Pushing the Envelope for Polymer Flooding Towards High-temperature and High-salinity Reservoirs with Polyacrylamide Based Terpolymers," SPE 141497, Society of Petroleum Engineers (SPE), presented at SPE Middle East Oil and Gas Show and Conference, Mar. 20-23, 2011, 9 pages.

Vollrath et al., "Fluorescence imaging of cancer tissue based on metal-free polymeric nanoparticles—a review." J. Mater. Chem. B 1:15 (1994-2007), 2013, 15 pages.

Wagner, "The Use of Tracers in Diagnosing Interwell Reservoir Heterogeneities—Field Results," SPE-6046, Society of Petroleum Engineers (SPE), Journal of Petroleum Technology, Nov. 1997, 7 pages.

Wahajuddin et al., "Superparamagnetic iron oxide nanoparticles: Magnetic nanoplatforms as drug carriers" International Journal of Nanomedicine, 7, Jul. 2012, 3445-3471, 27 pages.

Walther et al, "Janus Particles: Synthesis, Self-Assembly, Physical Properties and Applications," American Chemical Society (ACS Publications), Chem. Rev. 113:7 (5194-5261), Apr. 2013, 68 pages.

Wampler, "Chapter 1: Applied pyrolysis: an overview," Applied Pyrolysis Handbook, 2007, 26 pages.

Wang et al., "Fabrication of Near Infrared Photonic Crystals using Highly-Monodispersed Submicrometer SiO2 Spheres," J. Phys. Chem. B 2003, 107 (44), 12113-12117.

Wang et al., "Fabrication of Two- and Three-Dimensional Silica Nanocolloidal Particle Arrays," J. Phys. Chem. B, 2003, 107(15): 3400-3404, 5 pages.

Wang et al., "Self-assembly of two and three-dimensional particle arrays by manipulating the hydrophobicity of silica nanospheres," Journal of Physical Chemistry, Nov. 2005, 109(47): 22175-22180, 6 pages.

Wang et al., "The Design and Implementation of a Full Field Inter-Well Tracer Program on a Giant UAE Carbonate Oil Field," SPE-177527-MS, Society of Petroleum Engineers (SPE), in Abu Dhabi International Petroleum Exhibition and Conference, Nov. 2015, 8 pages.

Wang et al., "Toward Reservoir on a Chip: Fabricating Reservoir Micromodels by in Situ Growing Calcium Carbonate Nanocrystals in Microfluidic Channels," ACS Applied Materials and Interfaces, 2017, 21 pages.

Wever et al., "Polymers for enhanced oil recovery: A paradigm for structure-property relationship in aqueous solution," Progress in Polymer Science, 36:11 (1558-1628), Nov. 2011, 71 pages.

Wu et al., "Development of New Polymers with Better Performance under Conditions of High Temperature and High Salinity," SPE 155653, Society of Petroleum Engineers (SPE), presented at the SPE EOR Conference at Oil and Gas, Apr. 16-18, 2012, 11 pages.

Wu et al., "A reusable biosensor chip for SERS-fluorescence dual mode immunoassay," Proc. SPIE 9543: 954317-1, presented at the Third International Symposium on Laser Interaction with Matter (LIMIS), May 4, 2015, 6 pages.

Wu et al., "A SERS-Assisted 3D Barcode Chip for High-Throughput Biosensing," Material Views Full Papers, Small Journal 11:23 (2798-2806), Jun. 11, 2015, 9 pages.

Xu et al., "Superparamagnetic Photonic Crystals" Adv. Mater., Nov. 2001, 13, 1681-1683, 4 pages.

Xu et al., "Synthesis and Utilization of Monodisperse Superparamagnetic Colloidal Particles for Magnetically Controllable Photonic Crystals" Chem. Mater., 14(3), 2002, 1249-1256, 8 pages.

Xu et al., "Measurement of two-photon excitation cross sections of molecular fluorophores with data from 690 to 1050 nm," Journal of the Optical Society of America B 13:3, Mar. 1996, 11 pages.

Yang et al., "Nanoscale geochemical and geomechanical characterization of organic matter in shale," Nature Communications, vol. 8, 2179, Dec. 19, 2017, 9 pages.

Yang et al., "The Co-Luminescence Groups of Sm—La-pyridyl Carboxylic Acids and the Binding Characteristics between the Selected Doped Complex and Bovine Serum Albumin," Bulletin of the Korean Chemical Society 33:4 (1303-1309), Apr. 20, 2012, 7 pages.

Yang et al., "Paramagnetic labeling of proteins and pseudocontact shift in structural biology," Chinese Journal of Magnetic Resonance, 2014, 31:2 (155-171), English Abstract.

Ye et al., "Synthesis and Characterization of a Water-Soluble Sulfonates Copolymer of Acrylamide and N-Allylbenzamide as Enhanced Oil Recovery Chemical," Journal of Applied Polymer Science, 128:3, (2003-2011), May 5, 2013, 9 pages.

Yu et al., "Adsorption of proteins and nucleic acids on clay minerals and their interactions: A review" Applied Clay Science, 80-81, Aug. 2013, 443-452, 10 pages.

Yu et al., "New insights into flow physics in the EOR process based on 2.5D reservoir micromodels," Journal of Petroleum Science and Engineering, Jun. 2019, 181, XP085751272, 13 pages.

Yun et al., "Toward Reservoir on a Chip: Rapid Performance Evaluation of Enhanced Oil Recovery Surfactants for Carbonate Reservoirs Using a Calcite-Coated Micromodel," Nature Scientific Reports, 2020, 12 pages.

Zamberi et al., "Improved Reservoir Surveillance Through Injected Tracers In A Saudi Arabian Field: Case Study," SPE 166005, Society of Petroleum Engineers (SPE), presented at the SPE Reservoir Characterization and Simulation Conference and Exhibition, Sep. 16-18, 2013, 15 pages.

Zemel, "Chapter 3: Tracers in the Oil Field," in Tracers in the Oil Field, Technology and Engineering, Elsevier 43, Jan. 1995, 47 pages.

Zhang and Liu, "Mixed-mode chromatography in pharmaceutical and biopharmaceutical applications," Journal of Pharmaceutical and Biomedical Analysis, 2016,128: 73-88, 16 pages.

Zhang et al., "Effect of Concentration on HPAM Retention in Porous Media," SPE-166265-PA, Society of Petroleum Engineers (SPE), presented as SPE Annual Technical Conference and Exhibition, 373-380, Sep. 30-Oct. 2, 2013, 11 pages.

Zhang et al., "Janus Particles: Synthesis, Self-Assembly, Physical Properties, and Applications," American Chemical Society (ACS Publications), Langmuir 33: 6964-6977, 2017, 14 pages.

Zhang et al., "Novel zwitterionic surfactant derived from castor oil and its performance evaluation for oil recovery," Colloids Surfaces A: Physicochemical and Engineering Aspects 483: 87-95, 2015, 42 pages.

Zhang et al., "Water adsorption on kaolinite and illite after polyamine adsorption" Journal of Petroleum Science and Engineering, 142, Jun. 2016, 13-20, 8 pages.

Zhang et al., "Geomaterial-Functionalized Microfluidic Devices Using a Universal Surface Modification Approach," Advanced Material Interfaces, 2019, 6:23, 16 pages.

Zhao et al., "Chromatographic Separation of Highly Soluble Diamond Nanoparticles Prepared by Polyglycerol Grafting," Angewandte Chemie International Edition, 50:6 (1388-1392), Feb. 7, 2011, 5 pages.

(56) References Cited

OTHER PUBLICATIONS

Zheng et al., "Immobilization of Candida rugosa lipase on hydrophobic/strong cation-exchange functional silica particles for biocatalytic synthesis of phytosterol esters." Bioresource technology 115, Jul. 2012, 141-146, 6 pages.

Zhou et al., "Upconversion luminescent materials: advances and applications," American Chemical Society (ACS Publications), Chemical Reviews, 115: 395-465, Jan. 14, 2015, 71 pages.

\* cited by examiner

DETERMINING PARTITION COEFFICIENTS OF TRACER ANALYTES

TECHNICAL FIELD

This disclosure relates to determining partition coefficients.

BACKGROUND

The Environmental Protection Agency (EPA) uses partition coefficients to predict the environmental fate, aquatic toxicity, and bioaccumulation of chemicals and pollutants. The partition coefficient of tracers for oil reservoirs is defined by the ratio of tracer concentrations in the oil and water phases at equilibrium.

The partition coefficient is defined as the ratio of concentrations of a compound in a mixture of two immiscible solvents at equilibrium. Several methods for determining the partition coefficient are commonly used, for example, the static or "shake-flask" method, and the coreflooding method.

SUMMARY

This disclosure describes technologies relating to determining partition coefficients of tracer analytes.

An example of the subject matter described within this disclosure is a method with the following features. Optical properties of a tracer in water are measured at varying concentrations. A reference curve is built based on the measured optical properties at varying concentrations. An emulsion is mixed with the tracer. The emulsion is demulsified into an oil component and an aqueous component. Optical properties of one of the components are measured. A partition coefficient is determined based on the measured optical properties of a demulsified component and the reference curve.

Aspects of the example method, which can be combined with the example method alone or with other aspects, can include the following. The measured component is the aqueous component.

Aspects of the example method, which can be combined with the example method alone or with other aspects, can include the following. Mixing includes static mixing.

Aspects of the example method, which can be combined with the example method alone or with other aspects, can include the following. Mixing the emulsion with the tracer includes receiving the emulsion and the trace by a microfluidic chip.

Aspects of the example method, which can be combined with the example method alone or with other aspects, can include the following. Demulsifying the emulsion includes flowing the mixed emulsion and tracer through a membrane separator.

Aspects of the example method, which can be combined with the example method alone or with other aspects, can include the following. The optical properties include ultraviolet visibility or fluorescence intensity.

Aspects of the example method, which can be combined with the example method alone or with other aspects, can include the following. The tracers include at least of one of the following: dipicolinic acid, chelidamic acid, 4-chloropyridine-2,6-dicarboxylic acid, 1,5-naphthalenedisulfonate, 2-fluorobenzoic acid, or 4-Chlorobenzyl alcohol.

Aspects of the example method, which can be combined with the example method alone or with other aspects, can include the following. Measuring the optical properties includes exposing a sample to light at 214 nanometer wavelength.

Aspects of the example method, which can be combined with the example method alone or with other aspects, can include the following. Measuring the optical properties comprises measuring a visibility or fluorescent intensity of the sample responsive to exposing the sample to light.

An example of the subject matter described within this disclosure is a system with the following features. A microfluidic mixing chip, a separator, an optical detection system, and a controller are all included. The controller is configured to send a signal to a separation system. The signal is a command to begin a separation process. The controller is configured to receive a measurement signal from an optical detector. The measurement signal is indicative of a concentration of a tracer within a sample. The controller is configured to compare the measurement signal to a known dataset of tracer concentrations. The controller is configured to determine a partition coefficient based on the comparison of the measurement signal with the dataset.

Aspects of the example system, which can be combined with the example system alone or with other aspects, can include the following. The controller is further configured to activate a light source emitting a light at 214 nanometer wavelength or 254 nanometer wavelength.

Aspects of the example system, which can be combined with the example system alone or with other aspects, can include the following. The separator is a membrane separator.

Aspects of the example system, which can be combined with the example system alone or with other aspects, can include the following. The optical detection system includes a light sensor.

Aspects of the example system, which can be combined with the example system alone or with other aspects, can include the following. The optical detection system includes a controllable light source emitting light at 254 nanometer wavelength.

An example of the subject matter described within this disclosure is a method with the following features. Optical properties of an aqueous tracer in water are measured at varying concentrations. Based on the measured optical properties at varying concentrations, a reference curve is developed. An emulsion is mixed with the aqueous tracer by a microfluidic chip. The emulsion is demulsified by a membrane separator. Optical properties of a demulsified component are measured. A partition coefficient is determined based on the measured optical properties of the demulsified components and the developed reference curve.

Aspects of the example method, which can be combined with the example method alone or with other aspects, can include the following. Measuring the optical properties includes exposing a sample to light at 214 nanometer wavelength or 254 nanometer wavelength.

Aspects of the example method, which can be combined with the example method alone or with other aspects, can include the following. Measuring the optical properties include measuring a visibility or fluorescent intensity of the sample responsive to exposing the sample to light.

Aspects of the example method, which can be combined with the example method alone or with other aspects, can include the following. The optical properties include ultraviolet visibility or fluorescence intensity.

Aspects of the example method, which can be combined with the example method alone or with other aspects, can include the following. The tracers include at least of one of the following: dipicolinic acid, chelidamic acid, 4-chloropyridine-2,6-dicarboxylic acid, 1,5-naphthalenedisulfonate, 2-fluorobenzoic acid, or 4-Chlorobenzyl alcohol.

Aspects of the example method, which can be combined with the example method alone or with other aspects, can include the following. The demulsified component is an aqueous component.

Particular implementations of the subject matter described in this disclosure can be implemented so as to realize one or more of the following advantages. The subject matter described herein allows for rapid determination of partition coefficients. The subject matter described herein can be used determine partition coefficients with much less solvent and analyte usage compared to the conventional methods.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

To save time and cost, microfluidic methods allow for a fast, portable, solventless, and sustainable device for determining partition coefficients. Molecular transport of the analyte between two immiscible phases is often controlled by diffusion. By decreasing the characteristic length of diffusion, time required to complete the experiment is also reduced. The time scale is imposed by the short diffusion length of the analyte across two phases and large specific interfacial area.

This disclosure describes a system and method for quickly determining partition coefficients of desired analytes with significantly reduced time compared to traditional methods, such as the shaker method. The system and methods include mixing an emulsion and a tracer upon a microfluidic chip. The emulsification is then demulsified and the concentration of the tracer is measured in either the water phase or the oil phase (depending on which analyte is used). An optical property of the tracer is measured with an optical detector. The measurements detected by the optical detector are then compared to known optical measurements to determine a partition coefficient of the tracer.

Figure 1:
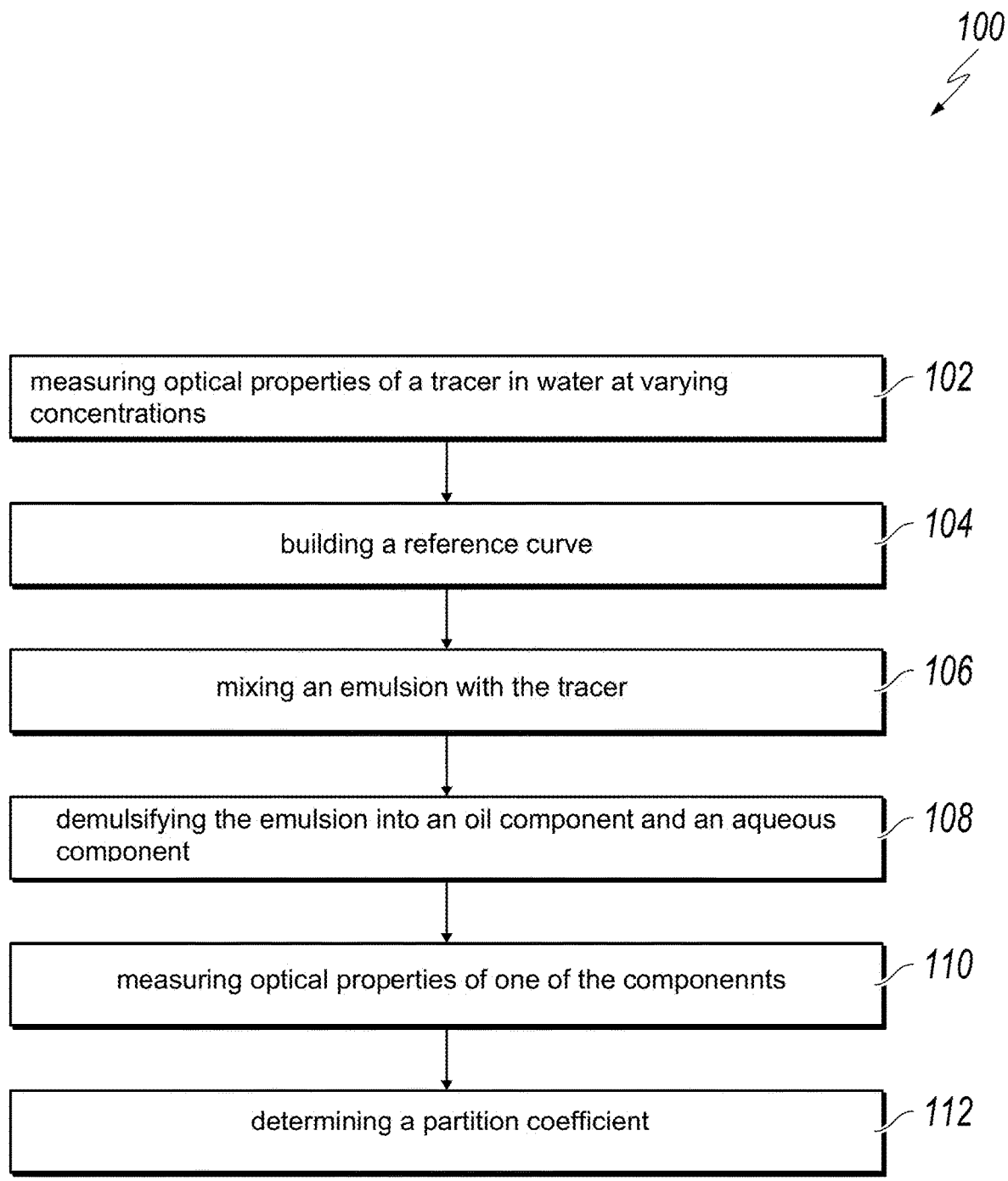
FIG. 1 is a flowchart of a method that can be used with aspects of this disclosure.

FIG. 1 is a flowchart of a method 100 that can be used with aspects of this disclosure. In particular, the methods described herein can be used to determine the partition coefficient of analytes on the order of minutes. At 102, optical properties of a tracer in water are measured at varying concentrations. In some implementations, optical properties can include visibility at various wavelengths, such as ultraviolet visibility or short, medium, and long-wave infrared. In some implementations, optical properties include fluorescence intensity, or amplitude, with or without stimulation. In instances where stimulation is used, stimulation can include stimulation by a wavelength of light, for example, stimulation light at 214 nanometer wavelength or 254 nanometer wavelength. Tracers that can be used with aspects of this disclosure include dipicolinic acid; chelidamic acid, 4-chloropyridine-2,6-dicarboxylic acid, 1,5-naphthalenedisulfonate, 2-fluorobenzoic acid, or, 4-Chlorobenzyl alcohol. Other tracers beyond those explicitly listed or described within this disclosure can be used without departing from this disclosure.

Figure 2:
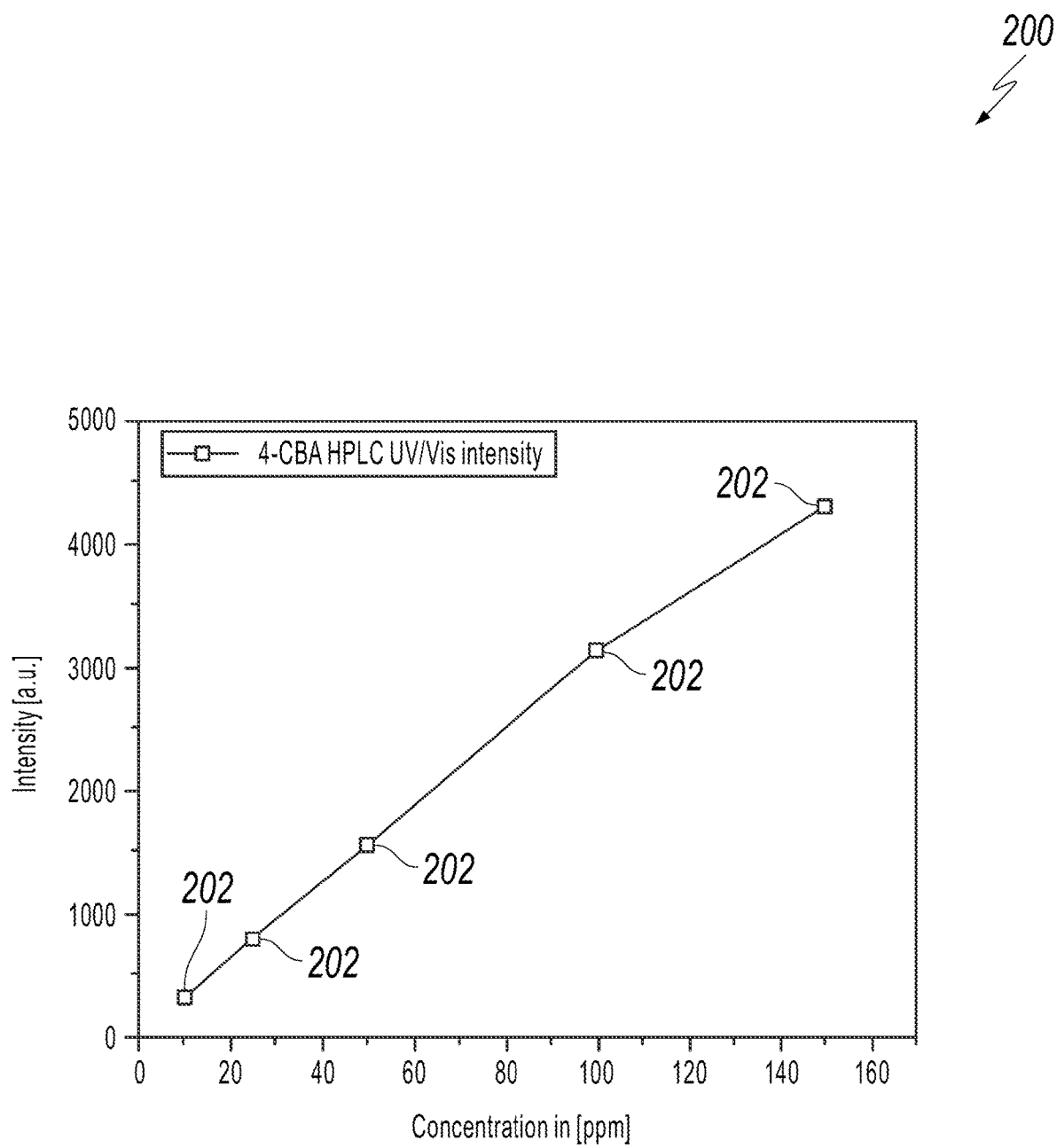
FIG. 2 is an example reference curve that can be used with aspects of this disclosure.

At 104, based on the measured optical properties at varying concentrations, a reference curve is built. FIG. 2 illustrates an example of such a reference curve 200. To develop this curve, a sample with a first amount of tracer is measured and recorded. Subsequent samples with varying concentrations are similarly measured to develop the reference points 202 seen on the curve 200. In some implementations, the tracer is an aqueous tracer mixed with water at various concentrations for each of the samples. This curve 200 is later used as a reference point for the remainder of the method steps. Method steps 102 and 104 can be performed in advance of the remaining steps to develop an initial reference curve 200. Multiple reference curves 200 for multiple tracers can be developed and stored for reference at a later date.

Figure 3:
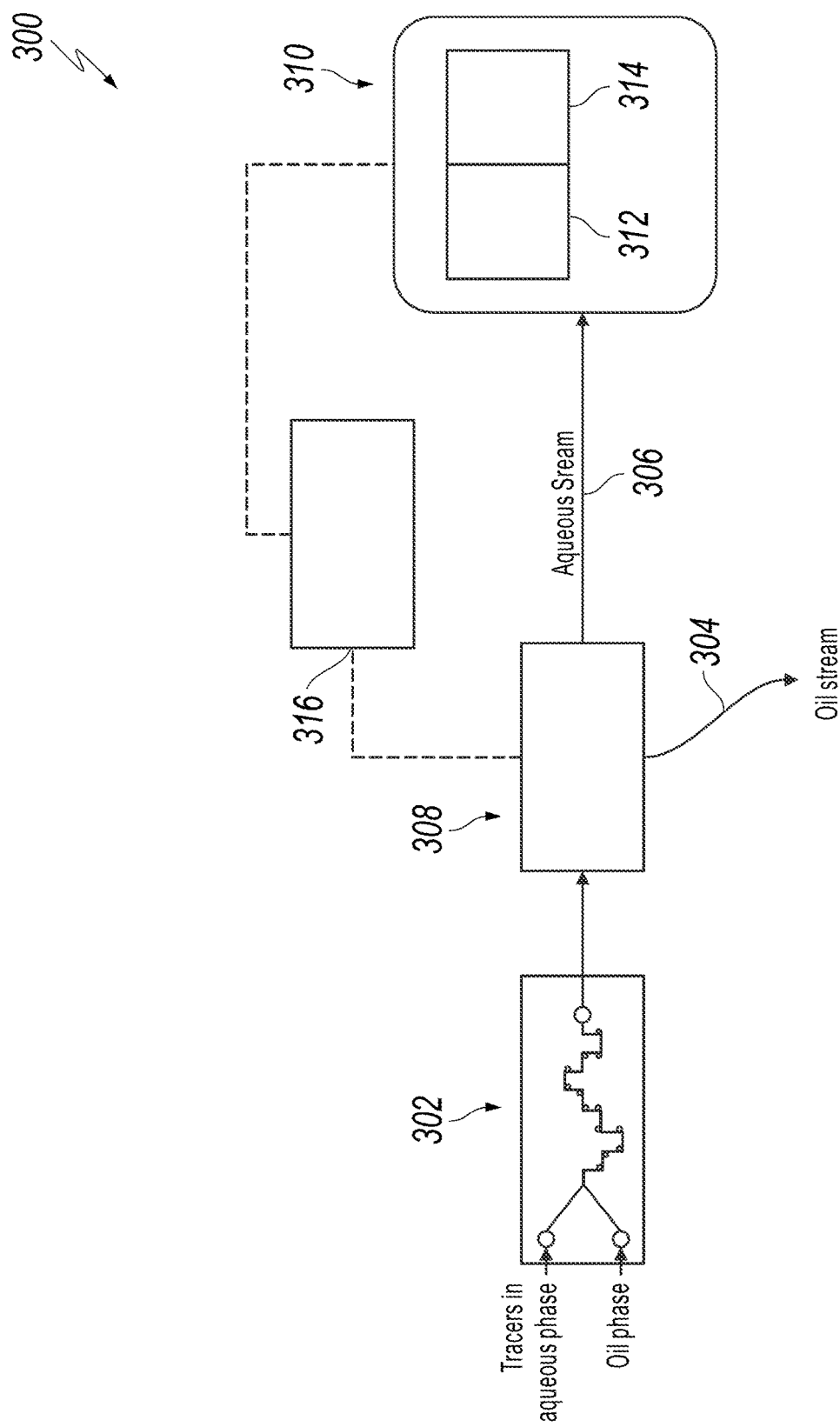
FIG. 3 is a schematic diagram of an example analysis system that can be used with aspects of this disclosure.

Referring back to FIG. 1, at 106, an emulsion and a tracer are mixed with one another. In some implementations, the tracer is an aqueous tracer. The remainder of the method 100 will be described in the context of FIG. 3, which is a schematic diagram of an example analysis system 300 that can be used with aspects of this disclosure.

In some implementations, a microfluidic chip 302 (see FIG. 3) can be used. While this disclosure primarily references and describes using a microfluidic chip for mixing, several different mixing techniques can be used without departing from this disclosure. For example, sonication or dynamic shakers can be used without departing from this disclosure.

In an example procedure, 3 ml of tracer dissolved water solution (100 ppm) is injected into a teardrop microfluidic mixing chip using a syringe pump with a flow rate 0.5 ml/min. Using a separate syringe pump, a 1 ml pulse of crude oil is concurrently injected with the aqueous solution. The various fluid components are thoroughly mixed in a microfluidic mixing chip. This example procedure makes apparent the small quantities of fluids needed to determine a partition coefficient.

After the emulsion and tracer are mixed with one another, at 108, the emulsion is demulsified into an oil component 304 and an aqueous component 306. In some implementations, demulsion is done mechanically. That is, additional chemical demulsifiers are not added. Rather, for example, a membrane separator 308 is used. In some implementations, other demulsification techniques can be used. For example, a hydrocyclone or centrifugal separator can be used to demulsify the mixture without departing from this disclosure.

At 110, optical properties of one of the components are measured. In the illustrated implementation, the water component is measured. Such a scenario can occur, for example, when an aqueous tracer is used. In some implementations, the oil component is measured. In such an implementation, the oil component 304 is directed into a measuring apparatus, or optical detector 310, in lieu of the aqueous component 306.

In some implementations, the optical properties are measured by an optical detection system 310. In some implementations, measuring optical properties includes exposing the component sample or stream to a specified wavelength of light. For example, the sample or stream can be exposed to light source 312 emitting light at 214 nanometer wavelength or 254 nanometer wavelength. In such implementations, a light source 312 emitting other specified wavelengths of light can be used. Implementations using such a light source can be used, for example, in instances where measuring the optical properties includes measuring a visibility or fluorescent intensity of the sample responsive to exposing the sample to the specified wavelength of light. To measure such properties, the optical detection system includes a light sensor 314. The light sensor can be tuned to a single wavelength of light or a range or wavelengths. Depending upon the configuration, the optical sensor can be adjacent to the light source 312, perpendicular to the light source, or directly across from the light source. Other relative orientations of the light source 312 and light sensor can be used without departing from this disclosure. Regardless of orientation, the light source 312 and light sensor 314 are both arranged to shine towards a sample or stream being measured.

At 112, a partition coefficient of the tracer is determined based on the measured optical properties of a demulsified component and the reference curve 200. For example, the partition coefficient can be determined by comparing the fluorescence intensity of the sample or stream to the curve using the following equations:

$$K_{OW} = \frac{L_W}{L_O}\left[\frac{I_{W,initial} - I_{dark}}{I_{W,final} - I_{dark}} - 1\right] \quad (1)$$

$$K_{OW} = \frac{C_O}{C_W} \quad (2)$$

where, $K_{ow}$ is the partition coefficient, $L_o$ is a length of the octanol droplet in a microchannel of the microfluidic ship, $L_w$ is the length of a water droplet in the microchannel, $I_w$ is fluorescence intensity of the analytes in water, $I_{dark}$ is the fluorescence intensity of the channel without analytes, Co is the concentration of analytes in oil and Cw is the concentration of analytes in water. In some implementations, other optical properties and other equations can be used without departing from this disclosure. The optical detector 310, the membrane separator 308, or both, in some implementations, are coupled to a controller 316.

Figure 4:
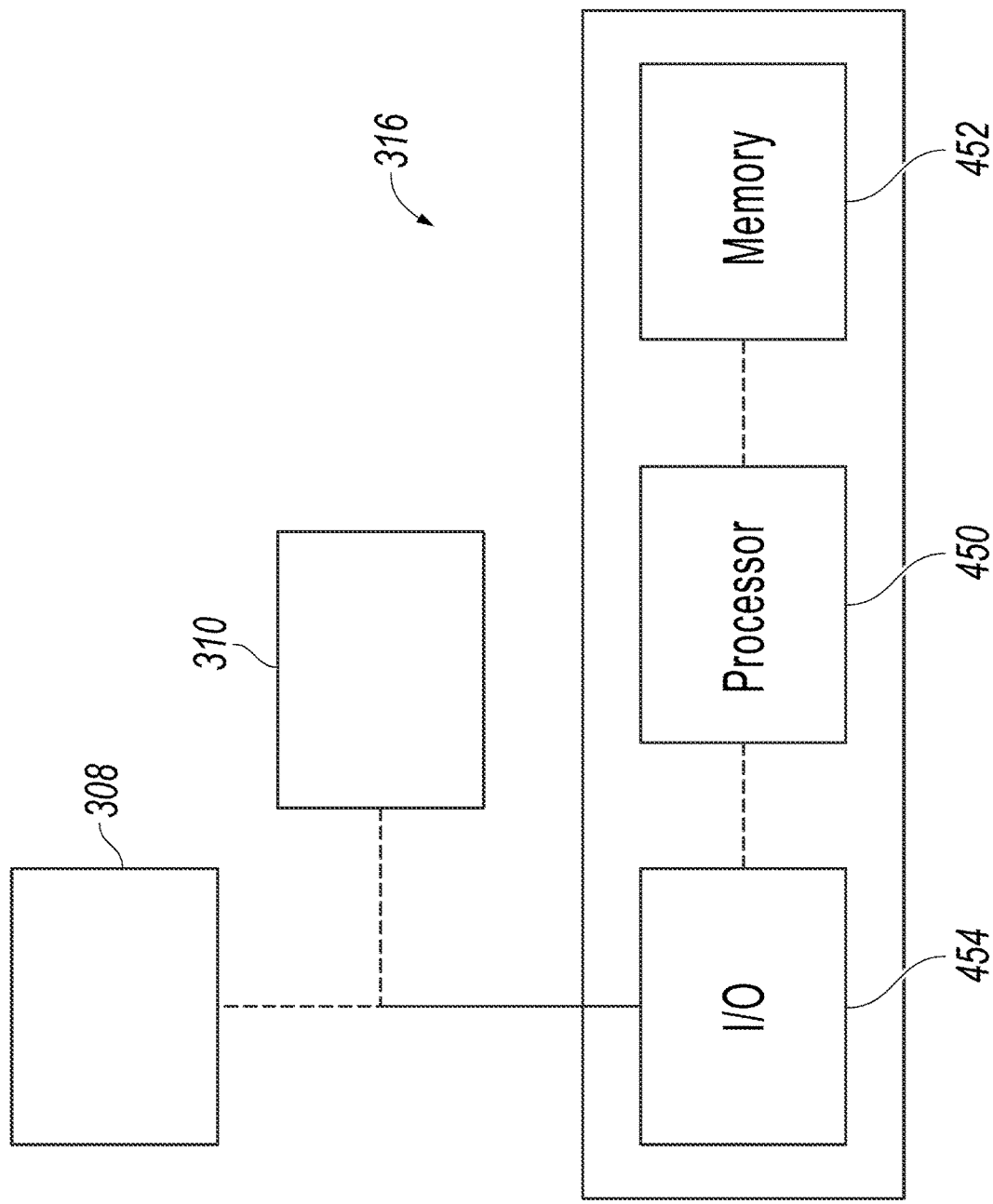
FIG. 4 is a schematic diagram of an example controller that can be used with aspects of this disclosure.

FIG. 4 is a schematic diagram of an example controller 316 that can be used with aspects of this disclosure. The controller 316 can, among other things, monitor parameters of the system 300 and send signals to actuate and/or adjust various operating parameters of the system 300. As shown in FIG. 4, the controller 316, in certain instances, includes a processor 450 (e.g., implemented as one processor or multiple processors) and a memory 452 (e.g., implemented as one memory or multiple memories) containing instructions that cause the processors 450 to perform operations described herein. The processors 450 are coupled to an input/output (I/O) interface 454 for sending and receiving communications with components in the system, including, for example, the light sensor 314. In certain instances, the controller 316 can additionally communicate status with and send actuation and/or control signals to one or more of the various system components (including an actuable systems, such as the light source 312 or the membrane separator 308) of the system 300, as well as other sensors (e.g., pressure sensors, temperature sensors, and other types of sensors) provided in the system 300. In certain instances, the controller 316 can communicate status and send control signals to one or more of the components within the system 300, such as the actuator light source 312. The communications can be hard-wired, wireless or a combination of wired and wireless. In some implementations, controllers similar to the controller 316 can be located elsewhere, such as in a data van, elsewhere on a site or even remote from the site. In some implementations, the controller 316 can be a distributed controller with different portions located about a site or off site. For example, in certain instances, the controller 316 can be located at the optical detector 310, or it can be located in a separate control room or data van. Additional controllers can be used throughout the site as stand-alone controllers or networked controllers without departing from this disclosure.

The controller 316 can operate in monitoring, commanding, and using the system 300 for measuring and determining partition coefficients of tracers. To make such determinations, the controller 316 is used in conjunction with the optical, or light sensor 314. Input and output signals, including the data from the sensor, controlled and monitored by the controller 316, can be logged continuously by the controller 316 within the controller memory 452 or at another location.

The controller 316 can have varying levels of autonomy for controlling the system 300. For example, the controller 316 can begin the method 100, and an operator adjusts the membrane separator 308 and optical detector 310. Alternatively, the controller 316 can begin the method 100, receive an additional input from an operator, and begin adjusting the membrane separator 308 and optical detector 310 with no other input from an operator. Alternatively, the controller 316 can begin the method 100 and adjust membrane separator 308 and optical detector 310 with no input from an operator.

Regardless of the autonomy of the controller operation, the controller can perform any of the following functions. The controller is configured to send a signal to the separator 308. The signal is a command to begin the separation process, demulsifying the emulsion. In some implementations, the controller 316 is configured to activate a light source emitting a light at 214 nanometer wavelength or 254 nanometer wavelength. A measurement signal is received by the controller 316 from an optical detector 310. The measurement signal is indicative of a concentration of a tracer within the measured sample or stream. The controller 316 then compares the measurement signal to a known dataset of tracer concentrations. The controller can then determine a partition coefficient based on the comparison of the measurement signal with the dataset.

While this disclosure contains many specific implementation details, these should not be construed as limitations on the scope of what may be claimed, but rather as descriptions of features specific to particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations described above should not be understood as requiring such separation in all implementations, and it should be understood that the described components and systems can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A method of determining a partition coefficient of a tracer, the method comprising:
    measuring optical properties of tracer solutions comprising varying concentrations of a tracer;
    providing a reference curve based on the measured optical properties of the tracer solutions;
    forming a mixed emulsion by mixing a pulse of crude oil and an aqueous solution comprising a known concentration of the tracer, wherein the mixing comprises:
        injecting the pulse of crude oil into a first inlet of a microfluidic chip using a first syringe pump, and
        injecting the aqueous solution into a second inlet of the microfluidic chip using a second syringe pump;
    the method further comprising demulsifying the formed mixed emulsion into an oil component and an aqueous component by flowing the formed mixed emulsion through a membrane separator;
    sending the oil component or the aqueous component to an optical measurement system external to the microfluidic chip; and
    measuring a component optical property of the oil component or of the aqueous component using the optical measurement system, the component optical property comprising a ultraviolet visibility or a fluorescence intensity, wherein the component optical property is indicative of a concentration of the tracer in the oil component or of a concentration of the tracer in the aqueous component;
    determining a partition coefficient of the tracer based on the measured component optical property and on the reference curve.

2. The method of claim 1, wherein the tracer comprises: dipicolinic acid; chelidamic acid; 4-chloropyridine-2; 6-dicarboxylic acid; 1,5-naphthalenedisulfonate; 2-fluorobenzoic acid; or 4-Chlorobenzyl alcohol.

3. A method of determining a partition coefficient of a tracer, the method comprising:
    measuring optical properties of aqueous tracer solutions comprising varying concentrations of a tracer;
    developing a reference curve based on the measured optical properties of the aqueous tracer solutions;
    forming a an emulsion by mixing a pulse of crude oil and an aqueous solution comprising a known concentration of the tracer using a microfluidic chip comprising an first inlet and a second inlet, the mixing comprising injecting 1 mL of the pulse of crude oil into the first inlet, and injecting 3 mL of the aqueous solution into the second inlet;
    forming a demulsified component by demulsifying the formed emulsion using a membrane separator;
    sending the demulsified component to an optical measurement system external to the microfluidic chip;
    measuring an optical property of the demulsified component using the optical measurement system, the optical property comprising a ultraviolet visibility or a fluorescence intensity and indicative of a concentration of the tracer in the demulsified component; and determining a partition coefficient of the tracer based on the measured optical property of the demulsified component and the developed reference curve.

4. The method of claim 3, wherein the measuring the optical property of the demulsified component comprises exposing the demulsified component to a light having a 214 nanometer wavelength or a 254 nanometer wavelength.

5. The method of claim 4, wherein the measuring the optical property of the demulsified component comprises measuring a visibility or a fluorescent intensity of the demulsified component responsive to the exposing.

6. The method of claim 3, wherein the tracer comprises: dipicolinic acid; chelidamic acid; 4-chloropyridine-2; 6-dicarboxylic acid; 1, 5-naphthalenedisulfonate; 2-fluorobenzoic acid; or 4-Chlorobenzyl alcohol.

7. The method of claim 3, wherein the demulsified component is an aqueous component.

8. The method of claim 3, wherein the demulsified component is an oil component.

9. The method of claim 1, wherein the optical property comprises a fluorescence intensity.

10. The method of claim 1, wherein demulsifying the formed mixed emulsion is performed mechanically.

* * * * *